United States Patent
Ishii et al.

(10) Patent No.: US 8,750,732 B2
(45) Date of Patent: Jun. 10, 2014

(54) MOISTURE SENSOR, MOISTURE DETECTOR, AND IMAGE FORMING APPARATUS

(75) Inventors: Toshihiro Ishii, Miyagi (JP); Yoshihiro Oba, Miyagi (JP); Fumikazu Hoshi, Miyagi (JP); Satoru Sugawara, Miyagi (JP)

(73) Assignee: Ricoh Company, Limited, Tokyo (JP)

( * ) Notice: Subject to any disclaimer, the term of this patent is extended or adjusted under 35 U.S.C. 154(b) by 110 days.

(21) Appl. No.: 13/604,845

(22) Filed: Sep. 6, 2012

(65) Prior Publication Data

US 2013/0057861 A1 Mar. 7, 2013

(30) Foreign Application Priority Data

Sep. 7, 2011 (JP) .................................. 2011-194495

(51) Int. Cl.
*G03G 15/00* (2006.01)

(52) U.S. Cl.
USPC ......................... 399/44; 356/450; 324/754.23

(58) Field of Classification Search
USPC .......................................... 356/340; 324/754
See application file for complete search history.

(56) References Cited

U.S. PATENT DOCUMENTS

| | | | | |
|---|---|---|---|---|
| 5,013,403 A | * | 5/1991 | Chase | ............................... 162/49 |
| 2005/0180620 A1 | | 8/2005 | Takiguchi | |
| 2006/0243931 A1 | | 11/2006 | Haran et al. | |
| 2007/0116330 A1 | | 5/2007 | Takiguchi | |
| 2008/0118114 A1 | | 5/2008 | Takiguchi | |
| 2011/0038511 A1 | | 2/2011 | Takiguchi | |
| 2011/0303848 A1 | | 12/2011 | Jones et al. | |
| 2012/0134693 A1 | | 5/2012 | Hoshi et al. | |
| 2013/0028615 A1 | * | 1/2013 | Satoh et al. | ........................ 399/9 |

FOREIGN PATENT DOCUMENTS

| | | |
|---|---|---|
| JP | 06-294736 | 10/1994 |
| JP | 09-061351 | 3/1997 |
| JP | 09-105716 | 4/1997 |
| JP | 09-222361 | 8/1997 |
| JP | 10-260142 | 9/1998 |
| JP | 2003-331270 | 11/2003 |
| JP | 2008-539422 | 11/2008 |
| JP | 2010-536050 | 11/2010 |
| JP | 2012-127937 A | 7/2012 |
| JP | 2012-128393 | 7/2012 |
| JP | 2012-208103 A | 10/2012 |
| WO | WO2006/118619 A1 | 11/2006 |
| WO | WO2009/022126 A1 | 2/2009 |

* cited by examiner

*Primary Examiner* — Walter L Lindsay, Jr.
*Assistant Examiner* — Roy Y Yi
(74) *Attorney, Agent, or Firm* — Oblon, Spivak, McClelland, Maier & Neustadt, L.L.P.

(57) ABSTRACT

A moisture sensor for detecting moisture content of an object includes a light source to emit light having an infrared wavelength that is absorbed by water; an optical system to receive the light from the light source and output linearly polarized light having a first polarization direction in a direction toward the object, and to receive light scattered from the object and output linearly polarized light having a second polarization direction perpendicular to the first polarization direction in another direction other than the direction toward the object; and a photodetector to receive the linearly polarized light having the second polarization direction output from the optical system.

8 Claims, 22 Drawing Sheets

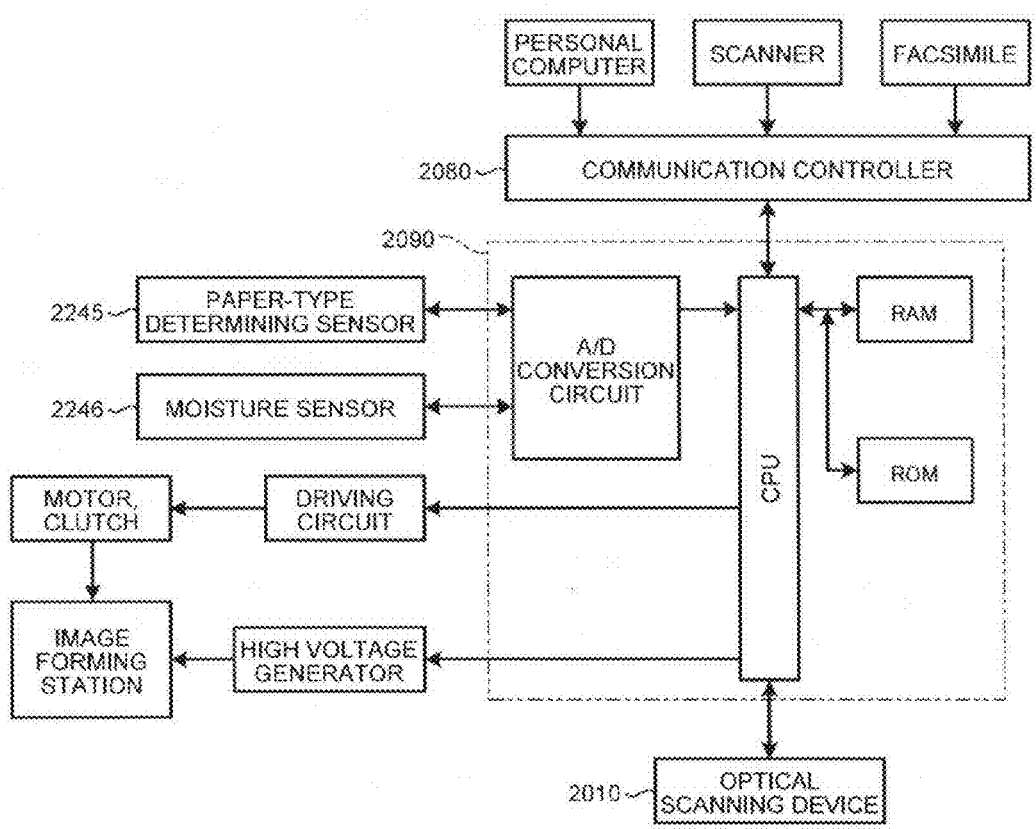
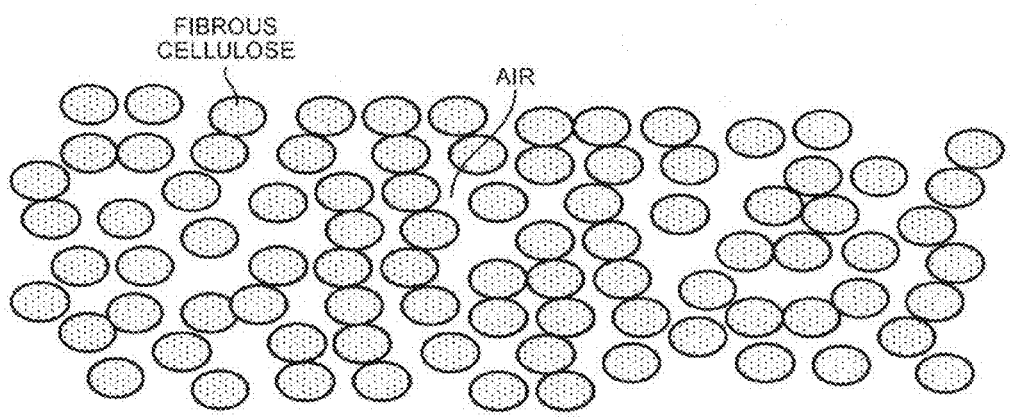

P-POLARIZED LIGHT

S-POLARIZED LIGHT

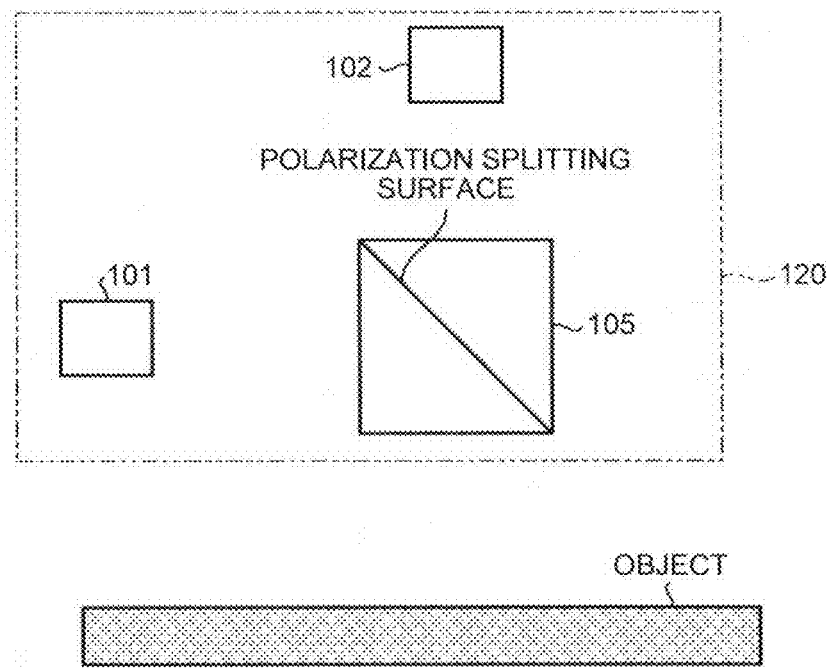

MOISTURE SENSOR, MOISTURE DETECTOR, AND IMAGE FORMING APPARATUS

CROSS-REFERENCE TO RELATED APPLICATIONS

The present application claims priority to and incorporates by reference the entire contents of Japanese Patent Application No. 2011-194495 filed in Japan on Sep. 7, 2011.

BACKGROUND OF THE INVENTION

1. Field of the Invention

The present invention relates to a moisture sensor, a moisture detector, and an image forming apparatus.

2. Description of the Related Art

In factories manufacturing foods or clothing, moisture sensors for detecting a moisture content of a product are used.

For example, Japanese Patent No. 3529516 discloses an optical measuring apparatus including a rotating plate that is installed obliquely to a light-projecting axis of a light source, has a filter and a reflector, and projects light onto a target of measurement through the filter when a measurement is to be conducted, a reflecting unit that folds and reflects the light reflected on the reflector included in the rotating plate so that the light passes through the filter on the rotating plate when no measurement is conducted, a collecting unit that collects the light from the target of measurement or the light from the reflecting unit and guides the light to a detecting element, and an operating unit that applies a correcting operation to an output of the detecting element.

Japanese Translation of PCT International Application Publication No. 2010-536050 discloses a method and an apparatus for electromagnetic detection for measuring parameters such as the moisture content or the basis weight of a fibrous web, e.g., paper or a non-woven.

Japanese Translation of PCT International Application Publication No. 2008-539422 discloses a sensor for measuring at least one component in a composition.

Japanese Patent No. 4499341 discloses a biometric authentication apparatus including an illuminating unit that outputs light having oscillation direction limited to one direction, and a blocking unit that blocks reflected light in a direction perpendicular to the oscillating direction of the light output from the illuminating unit.

Japanese Laid-open Patent Publication No. 10-260142 discloses an image evaluation apparatus including an illuminating unit that illuminates an image to be evaluated with parallel light rays having a linear polarization characteristic of either p-polarization or s-polarization, and a polarizing element that separates reflected light from the image to be evaluated into reflected light having a polarization plane that is on the same plane as the polarization plane of the illumination and reflected light having a polarization plane perpendicular to the polarization plane of the illumination.

Therefore, there is a need for a moisture sensor having a small size and providing high-precision measurement.

SUMMARY OF THE INVENTION

It is an object of the present invention to at least partially solve the problems in the conventional technology.

According to an embodiment, there is provided a moisture sensor for detecting moisture content of an object. The moisture sensor includes a light source to emit light having an infrared wavelength that is absorbed by water; an optical system to receive the light from the light source and output linearly polarized light having a first polarization direction in a direction toward the object, and to receive light scattered from the object and output linearly polarized light having a second polarization direction perpendicular to the first polarization direction in another direction other than the direction toward the object; and a photodetector to receive the linearly polarized light having the second polarization direction output from the optical system.

According to another embodiment, there is provided a moisture detector for detecting moisture content of paper. The moisture detector includes the moisture sensor according to the above embodiment, the object being the paper; a paper-type determining unit to determine a type of the paper; and a processor to correct an output of the moisture sensor based on a determination result of the paper-type determining unit.

According to still another embodiment, there is provided an image forming apparatus for forming an image on a recording medium. The image forming apparatus includes the moisture sensor according to the above embodiment, the object being the recording medium.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2 is a block diagram for explaining a configuration of a printer controller;

FIG. 3 is a schematic for explaining a model of paper;

FIG. 10 is a schematic for explaining an instrument 120;

DETAILED DESCRIPTION OF THE PREFERRED EMBODIMENTS

Figure 1:
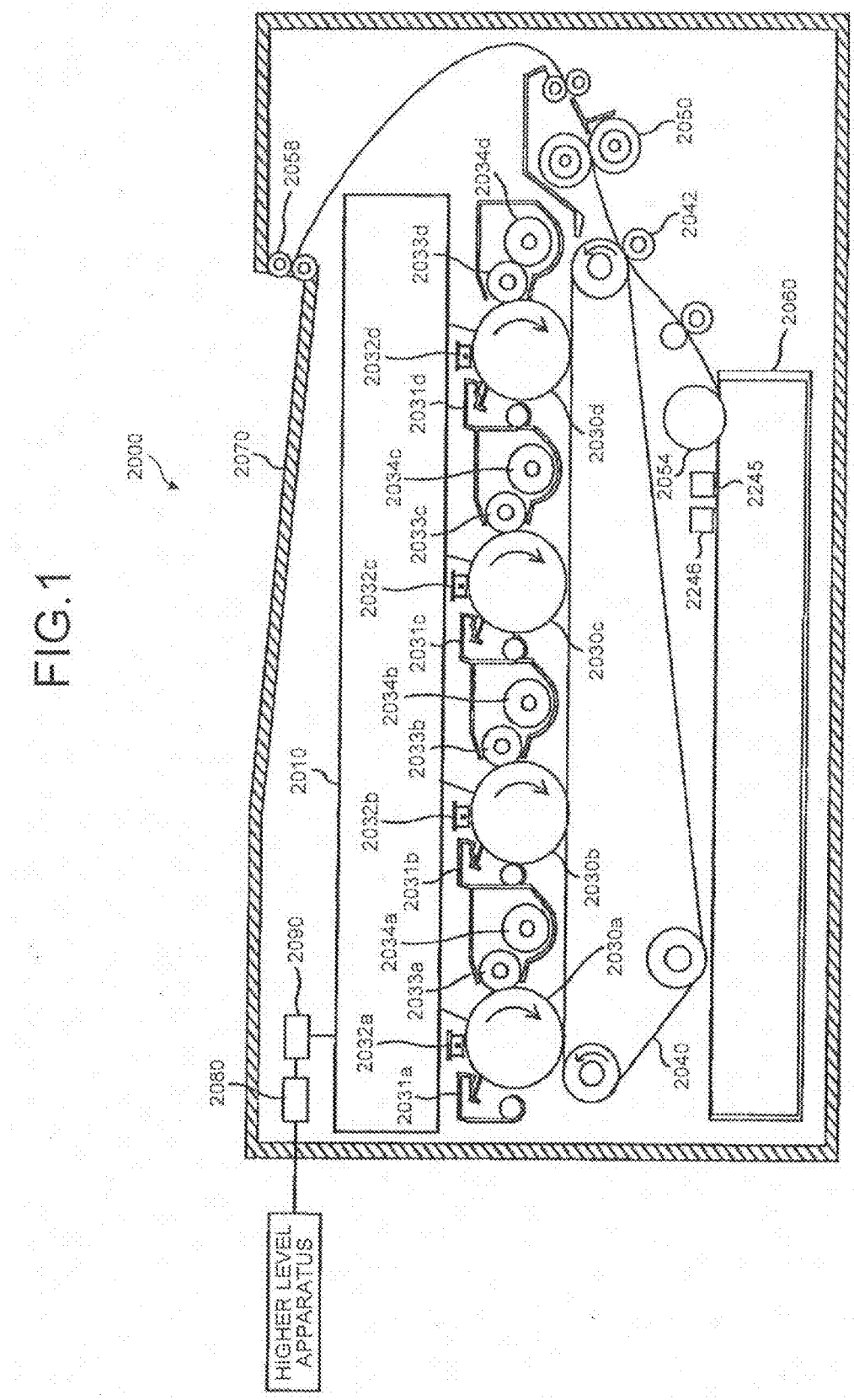
FIG. 1 is a schematic for explaining a general structure of a color printer 2000 according to an embodiment.

Embodiments of the present invention will now be explained with reference to FIGS. 1 to 29. FIG. 1 illustrates a general structure of a color printer 2000 according to an embodiment.

The color printer 2000 is a tandem type multi-color printer that forms a full-color image by printing four colors (black, cyan, magenta, and yellow) over one another. The color printer 2000 includes an optical scanning device 2010, four photosensitive drums (2030a, 2030b, 2030c, 2030d), four cleaning units (2031a, 2031b, 2031c, 2031d), four charging devices (2032a, 2032b, 2032c, 2032d), four developing rollers (2033a, 2033b, 2033c, 2033d), four toner cartridges (2034a, 2034b, 2034c, 2034d), a transfer belt 2040, transfer rollers 2042, a fixing unit 2050, a paper feeding roller 2054, discharging rollers 2058, a paper feed tray 2060, a discharge tray 2070, a communication controller 2080, a paper-type determining sensor 2245, a moisture sensor 2246, and a printer controller 2090 that controls each of these elements comprehensively.

The communication controller 2080 controls bidirectional communications with a higher-level apparatus (e.g., a personal computer) over a network or the like.

The printer controller 2090 includes a central processing unit (CPU), a read-only memory (ROM) storing therein computer programs described in a code interpretable by the CPU and various types of data used when the computer programs are executed, a random access memory (RAM) that is a working memory, and a digital-to-analog (A/D) conversion circuit that converts analog data into digital data (see FIG. 2). The printer controller 2090 controls each of the units in response to a request from the higher-level apparatus, and transmits image information received from the higher-level apparatus to the optical scanning device 2010.

The photosensitive drum 2030a, the charging device 2032a, the developing roller 2033a, the toner cartridge 2034a, and the cleaning unit 2031a are used as a set, and make up an image forming station for forming a black image (hereinafter also referred to as a "K station" for convenience).

The photosensitive drum 2030b, the charging device 2032b, the developing roller 2033b, the toner cartridge 2034b, and cleaning unit 2031b are used as a set, and make up an image forming station for forming a cyan image (hereinafter also referred to as a "C station" for convenience).

The photosensitive drum 2030c, the charging device 2032c, the developing roller 2033c, the toner cartridge 2034c, and the cleaning unit 2031c are used as a set, and make up an image forming station for forming a magenta image (hereinafter also referred to as an "M station" for convenience).

The photosensitive drum 2030d, the charging device 2032d, the developing roller 2033d, the toner cartridge 2034d, and the cleaning unit 2031d are used as a set, and makes up an image forming station for forming a yellow image (hereinafter also referred to as a "Y station" for convenience).

On the surface of each of the photosensitive drums, a photosensitive layer is formed. In other words, the surface of each of the photosensitive drums is a surface to be scanned. Each of the photosensitive drum is rotated by a rotating mechanism not illustrated, in the direction indicated by the arrow on the plane of FIG. 1.

Each of the charging devices charges the surface of the corresponding photosensitive drum uniformly.

The optical scanning device 2010 scans the charged surface of each of the photosensitive drums using a light beam modulated with each of the colors based on multi-colored image information (black image information, cyan image information, magenta image information, and yellow image information) received from the printer controller 2090. In this manner, a latent image corresponding to the image information is formed on the surface of each of the photosensitive drums. As each of the photosensitive drums is rotated, the latent image thus formed is moved toward the direction of the corresponding developing roller.

As the developing rollers are rotated, toner from each of the toner cartridges is applied to the corresponding developing roller thinly and uniformly. When the toner on the surface of each of the developing roller is brought into contact with the surface of the corresponding photosensitive drum, the toner is transferred onto a part of the photosensitive drum irradiated with light, and the toner adheres only to that part. In other words, each of the developing rollers visualizes the latent image formed on the surface of the corresponding photosensitive drum, by causing the toner to adhere to the surface of the photosensitive drum. As the photosensitive drum is rotated, the image on which the toner adhered (toner image) is moved to a direction of the transfer belt 2040.

Each of the yellow, the magenta, the cyan, and the black toner images is sequentially transferred onto the transfer belt 2040 at a given timing and superimposed over one another, so that a multi-colored color image is formed.

In the paper feed tray 2060, recording sheets are stored. The paper feeding roller 2054 is positioned near the paper feed tray 2060. The paper feeding roller 2054 takes out the recording sheets, one sheet at a time, from the paper feed tray 2060. The recording sheet is fed into a gap between the transfer belt 2040 and the transfer rollers 2042 at a given timing. In this manner, the color image on the transfer belt 2040 is transferred onto the recording sheet. The recording sheet transferred with the color image is then sent to the fixing unit 2050.

In the fixing unit 2050, heat and pressure are applied to the recording sheet, to fix the toner on the recording sheet. The recording sheet on which the toner is fixed is sent to the discharge tray 2070 via the discharging rollers 2058, and stacked on the discharge tray 2070 sequentially.

Each of the cleaning units removes the toner (residual toner) remaining on the surface of the corresponding photosensitive drum. The surface of the photosensitive drum having residual toner removed is then returned to a position facing the corresponding charging device.

The paper-type determining sensor 2245 is used to identify the brand of recording sheets stored in the paper feed tray 2060.

The moisture sensor 2246 is used to detect a moisture content ratio of the recording sheets stored in the paper feed tray 2060.

A moisture content ratio of an object will now be explained.

How to Evaluate Moisture Content Ratio

As expressed in Equations (1) and (2) below, a ratio of the intensity of scattered light (denoted as I) with respect to the intensity of incident light (denoted as $I_0$) on an object is in a relationship with a moisture content ratio (denoted as $N_d$) of the object, based on the Lambert-Beer law. Where, $R_e$ is the intensity of a surface reflected light, $B_g$ is the intensity of surface scattered light, α is a light absorption coefficient of water for light at a wavelength of 1.45 micrometers, and $L_d$ is a distance by which the light penetrated inside of the object propagates through the inside.

$$I/I_0 = \exp(\alpha \cdot d) + B_g + R_e \quad (1)$$

$$d = N_d \times L_d \quad (2)$$

Because paper as an object is very thin, e.g., with a thickness of approximately 100 micrometers, a change in the intensity of scattered light with respect to a change in the moisture content ratio is extremely small. In such a case, it is extremely difficult to detect the change in the scattered light intensity highly precisely, and the presence of noise components makes the measurement even more difficult. Such a noise component includes a noise caused by instability of the distance between the optical system and the object, and a noise in signals. The noise component caused by instability of the distance between the optical system and the object instabilizes the amount of light from the object surface.

Furthermore, the smoothness of the surface and a coating layer on the surface differ depending on paper types. Therefore, if the paper types are different, for example, the intensity of scattered light might be different, even when the moisture content ratio is the same.

In order to detect the moisture content ratio in paper more precisely, it is preferable to remove the scattered light on the surface (hereinafter shortly referred to as "surface scattered light") as much as possible, and to extend the optical path length of the light penetrated inside of the paper as much as possible. Hereinafter, the light penetrated inside of paper and scattered inside of the paper is shortly referred to as "internally scattered light".

The inventors observed scattering behaviors of light in paper, and investigated for a way for extending the length of the optical path inside of the paper. The inventors then discovered a method for selectively detecting internally scattered light at positions deep inside of paper. The experiments conducted and a physical model will be explained below in detail.

Scattering Model in Paper

Despite paper has a smooth surface, the surface has very small recesses and projections, when strictly observed. Therefore, when light is incident, the light is reflected by the recesses and the projections, in directions other than a specular direction. The light reflected to directions other than the specular direction is the surface scattered light.

In this model, the recesses and the protrusions are approximated with micro-facets, using the micro-facet theory that has been recently researched actively.

The major constituent of general paper is cellulose, which is a fibrous constituent produced from wood and the like. Cellulose is transparent and colorless in the wavelengths of visible light. There is also paper containing a large quantity of additives, such as calcium carbonate and kaolin, these additives are also transparent and colorless. Therefore, to facilitate easier understanding, paper is explained to be made of fibrous cellulose only.

In paper, fibrous cellulose in a length of several micrometers is laid over one another, and a layer structure of cellulose and the air is formed (see FIG. 3).

The surface of such paper can be considered to be a rough surface. On such a surface, when light is incident, the light becomes separated into the surface scattered light and the light penetrating inside of the paper.

Once the light penetrated inside of the paper reaches a cellulose surface, a part of the light is reflected on the cellulose surface, and the remaining light penetrates inside of the cellulose. A part of the light penetrated inside of the cellulose is reflected on the interface between the cellulose and the air, and the remaining light penetrates through the interface. The intensity of the light reflected on the interface between the cellulose and the air and the intensity of the light penetrated through the interface are determined only by a refractive index difference, the incident angle of the light on the interface, and the polarization direction of the light, based on the Fresnel's law, when the interface is assumed to be a microfacet surface.

The light reflected on the surface of the cellulose and the light penetrated through the interface become incident on the surface of another piece of cellulose. In this manner, the light penetrated inside of the paper scatters inside of the paper.

The light penetrated into and scattered deep inside of the paper has a long optical path that is the length by which the light propagates inside of the paper, and enables $L_d$ in Equation (2) to be increased. When the moisture content ratio is to be detected, detection sensitivity can be increased when $L_d$ is increased. In other words, a detection precision of the moisture content ratio can be improved.

Because the scattered light and the specular reflected light from the paper travel in different directions, the scattered light and the specular reflected light can be detected individually, by providing photodetectors at different positions. However, it is difficult to detect the surface scattered light and the internally scattered light from the paper individually simply by providing photodetectors at different positions.

To detect a moisture content ratio, it is preferable for a photodetector to receive the internally scattered light, especially the internally scattered light penetrated and scattered deep inside of the paper in a selective manner.

Figure 4:
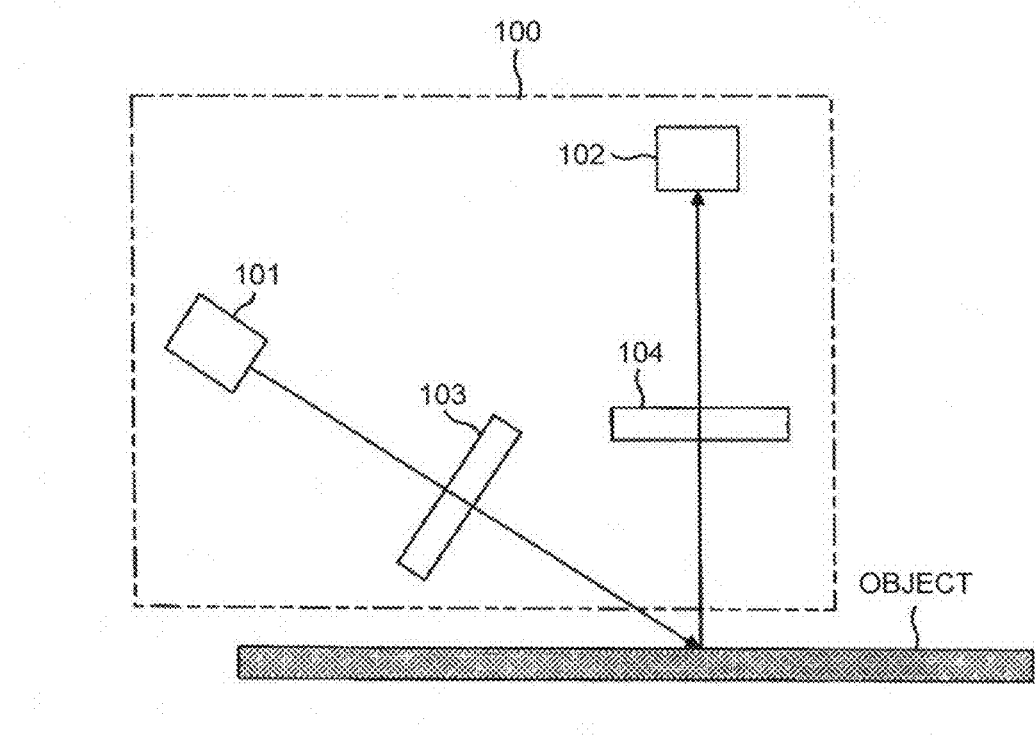
FIG. 4 is a schematic for explaining an instrument 100.

To understand conditions of the light inside of the paper, the inventors measured the intensity of scattered light from an object using an instrument 100 illustrated in FIG. 4. The instrument 100 includes a light emitting element 101, a photodetector 102, and two polarizers (103, 104).

Figure 5A:
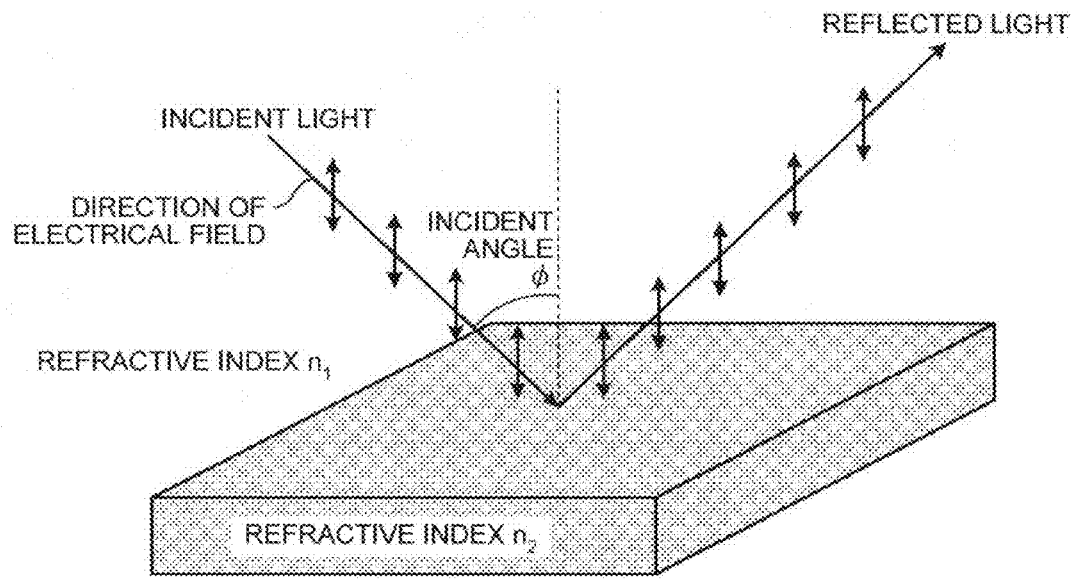
FIG. 5A is a schematic for explaining p-polarized light.
Figure 5B:
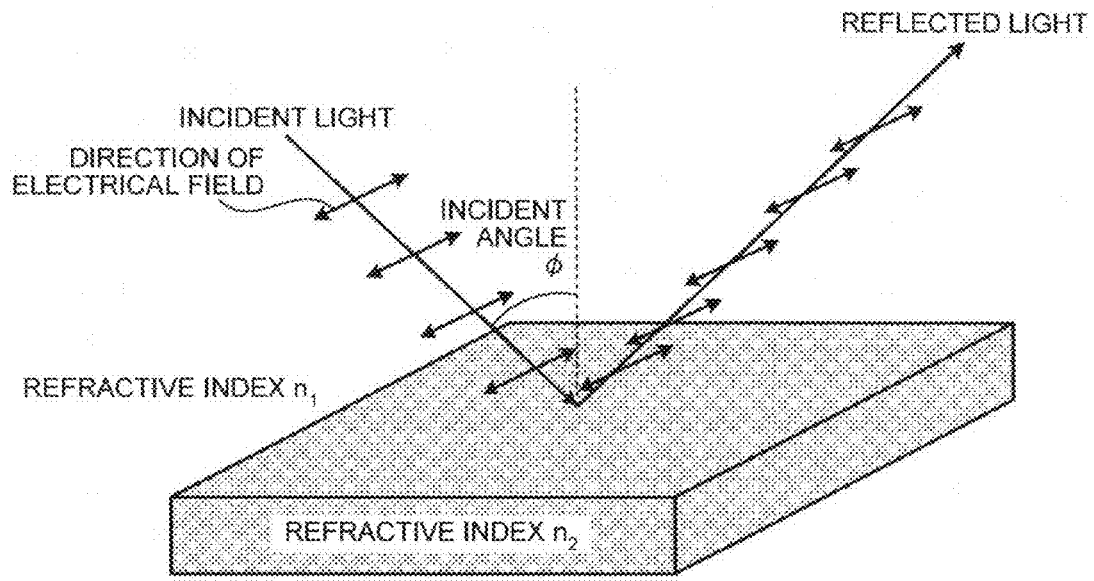
FIG. 5B is a schematic for explaining s-polarized light.

The polarizer 103 is disposed in the optical path of the light output from the light emitting element 101, and passes p-polarized light (see FIG. 5A). The object is then irradiated with the light passing through the polarizer 103. The polarizer 104 is positioned along the normal direction of the area of the object irradiated with the light, and passes s-polarized light (see FIG. 5B). The light passing through the polarizer 104 is received by the photodetector 102.

When a general light-scattering member was used as an object, a signal output from the photodetector 102 indicated that no light was detected. This indicates that the polarization direction of the surface scattered light hardly changed from the incident light.

Figure 6:
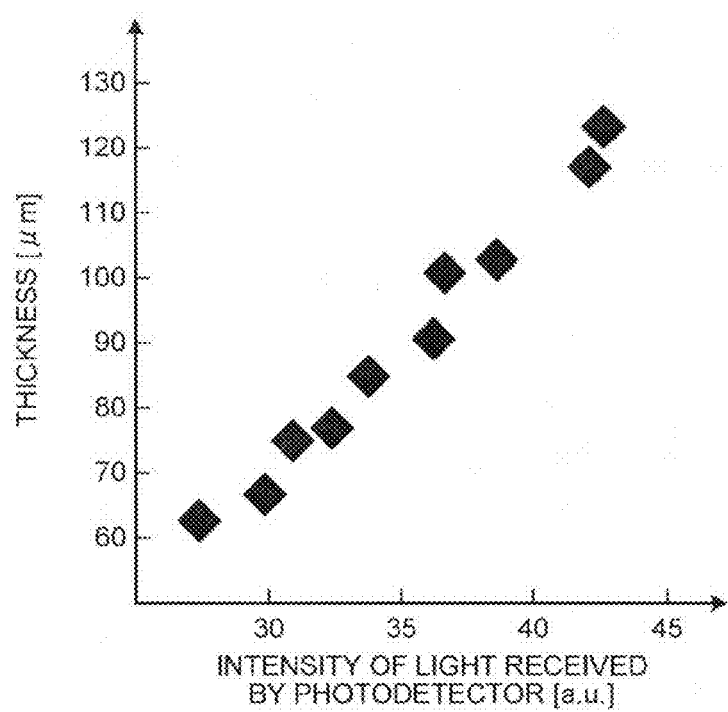
FIG. 6 is a schematic for explaining measurement results of the instrument 100.

The inventors then used several tens of paper types randomly selected from a plurality of paper types that are frequently used in general printers and copiers as objects, and measured the intensity of scattered light from the object using the instrument 100. The objects included standard paper having a smoothness between 20 seconds and 200 seconds, and coated paper having a smoothness exceeding several hundred seconds. The measurement results were as illustrated in FIG. 6. The thickness of the paper was measured using a micrometer. Based on these measurement results, the inventors found out that there was a high correlation between the amount of scattered light with a polarization direction rotated by 90 degrees with respect to the incident light and the paper thickness. In other words, the amount of scattered light having a polarization direction rotated by 90 degrees with respect to the incident light is increased for a paper type that is thicker.

Figure 7:
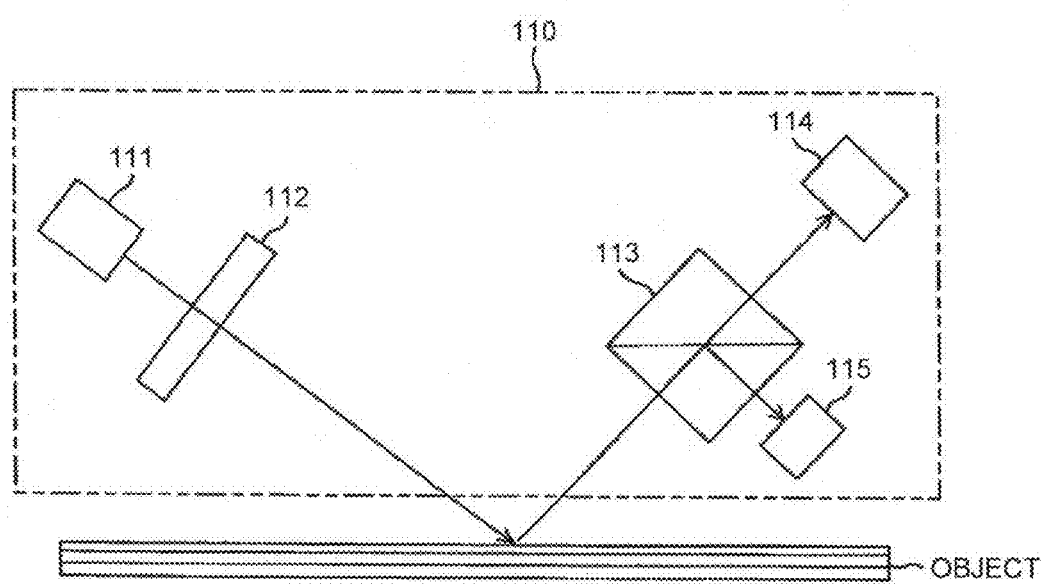
FIG. 7 is a schematic for explaining an instrument 110.

Paper Thickness and Component Having Polarization Direction Rotated by 90 Degrees from Incident Light To investigate thickness dependency of a polarization ratio, the intensity of scattered light from the object was detected using an instrument 110 illustrated in FIG. 7. The instrument 110 includes a light emitting element 111, a polarizer 112, a polarization beam splitter 113, and two photodetectors (114, 115).

The polarizer 112 is disposed in the optical path of the light from the light emitting element 111, and passes p-polarized light. An object is irradiated with the light passing through the polarizer 112 at an incident angle of 30 degrees. The polarization beam splitter 113 is disposed in the optical path of the light reflected on the object, and passes s-polarized light and reflects the p-polarized light. The light passing through the polarization beam splitter 113 is received at the photodetector 114, and the light reflected by the polarization beam splitter 113 is received by the photodetector 115. The amount of light received by the photodetector 114 divided by the amount of light received by the photodetector 115 represents a polarization ratio.

Figure 8:
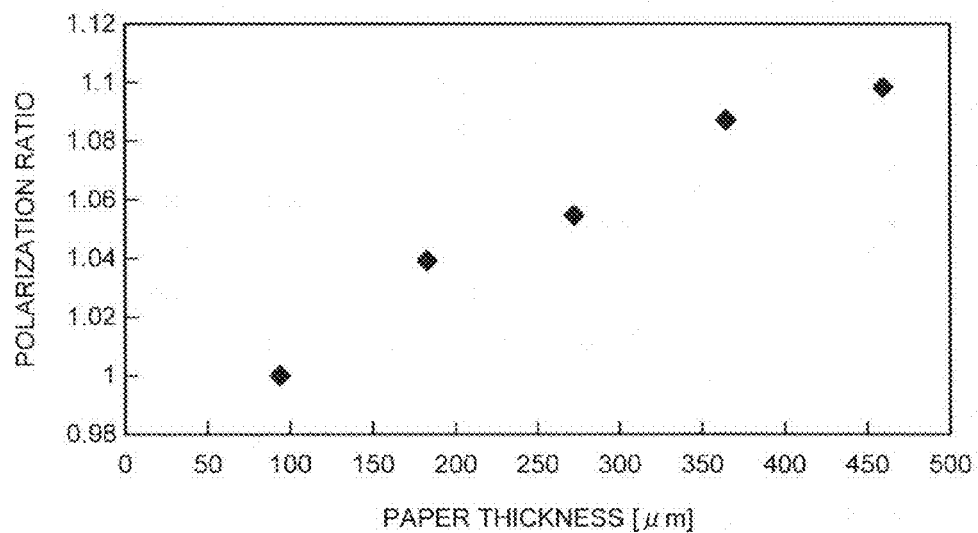
FIG. 8 is a schematic for explaining measurement results of the instrument 110.

As an object, standard paper with a smoothness of 33 seconds (My Recycle Paper manufactured by Ricoh Company, Ltd.) was used. The total thickness of a plurality of stacked sheets of the standard paper was used as a paper thickness. The measurement results were as illustrated in FIG. 8. In FIG. 8, the polarization ratio is standardized representing a result acquired for a single sheet of the standard paper (thickness 100 micrometers) as one.

It can be observed that, in FIG. 8, when the paper thickness increases, the polarization ratio increases as well, and the amount of light with a polarization direction rotated by 90 degrees with respect to the incident light increases as well. The same tendency was observed when other paper types were used as an object.

Figure 9:
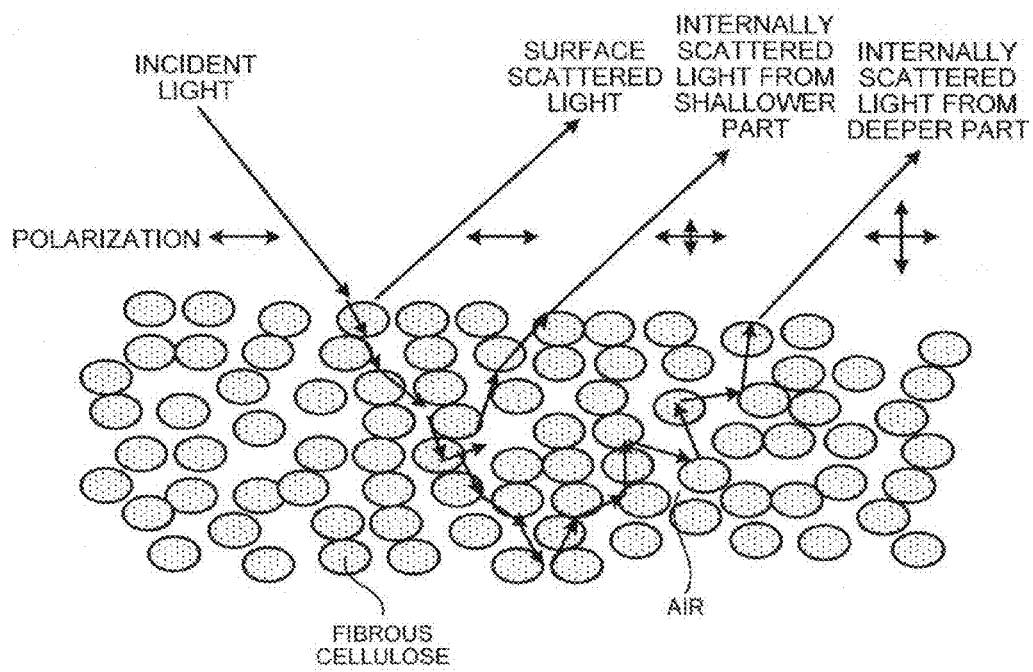
FIG. 9 is a schematic for explaining internally scattered light.

Therefore, it is possible to come up with a model in which internally scattered light from positions deeper inside of the paper is represented as light having a polarization direction rotated by 90 degrees with respect to incident light (see FIG. 9). The polarization direction of incident light scattered on the surface of the paper hardly changed from the incident light. By contrast, the light penetrated inside of the paper scatters repeatedly, causing the polarization direction to be rotated with respect to the incident light. The scattered light from positions deeper inside of the paper, having scattered more repeatedly, is more likely to have a polarization direction rotated by 90 degrees with respect to the incident light.

Optical System Enabling High Precision Detection

Based on the experiments and the observations described above, the inventors found out that internally scattered light and the surface scattered light can be separated taking advantage of the fact that the polarization direction is rotated by 90 degrees with respect to the incident light. In other words, the scattered light from deep inside of the paper can be filtered out by extracting only light having a polarization direction rotated by 90 degrees with respect to incident light. The scattered light from deep inside of the paper has a long optical path inside of the paper, and the scattered light with a long optical path inside of the paper has information related to a moisture content of the paper. Therefore, a high-precision moisture sensor can be achieved by separating light having polarization direction rotated by 90 degrees with respect to incident light, and receiving the light thus separated using a photodetector.

By taking advantage of the fact and using an optical system similar to the instrument 100, a detection precision of a moisture content ratio of paper can be improved, compared with a level conventionally achievable. In the instrument 100, the p-polarized light and the s-polarized light may be switched.

In the instrument 100, the photodetector 102 needs to be positioned somewhat away from the object so that the object is irradiated with the incident light. However if the photodetector 102 is positioned away from the object, the amount of light received by the photodetector 102 decreases, and the sensitivity might be reduced. Even when a condenser lens is to be provided in front of the photodetector 102, the same thing can be said because the condenser lens needs to be positioned away from the incident light. Furthermore, because polarizers are used in the instrument 100, costs are increased.

FIG. 10 depicts an instrument 120 in which a polarization beam splitter 105 is used instead of the two polarizers (103, 104) provided in the instrument 100. The polarization beam splitter 105 has a polarization splitting surface that reflects p-polarized light and passes s-polarized light.

Figure 11A:
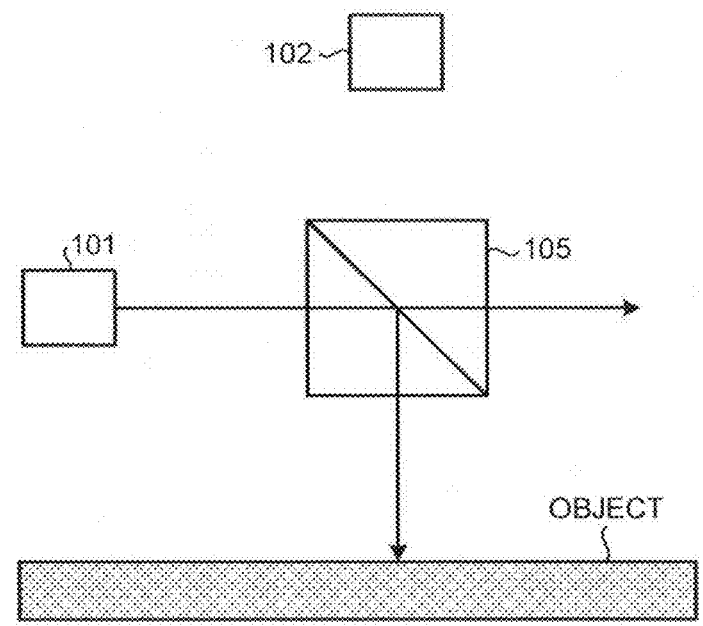
FIGS. 11A and 11B are schematics for explaining effects of a polarization beam splitter in the instrument 120.
Figure 11B:
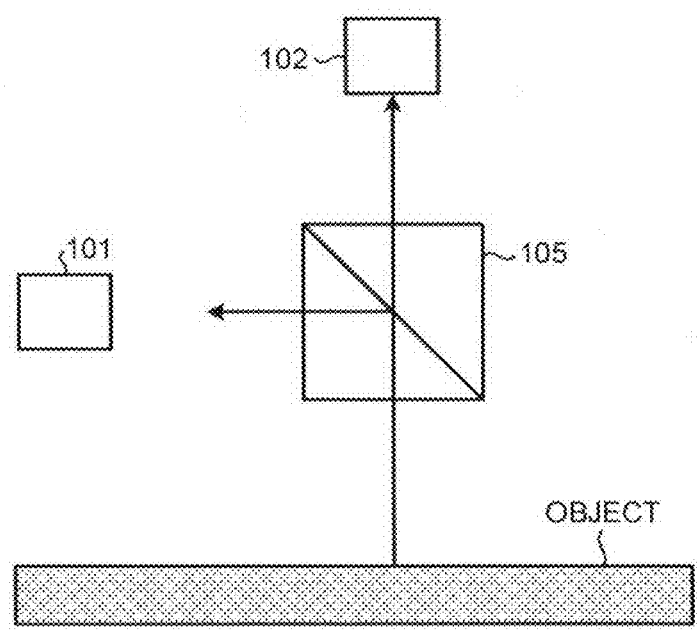
Figure 12:
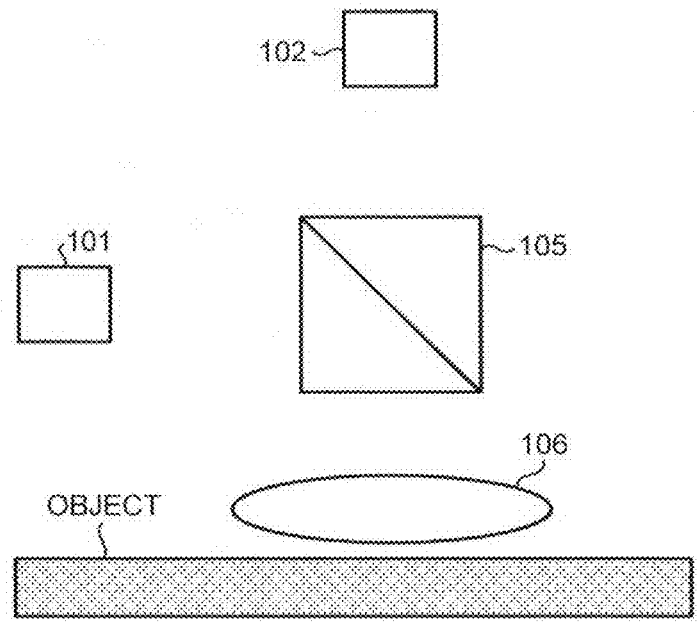
FIG. 12 is a schematic for explaining a condenser lens added to the instrument 120.

The object is then irradiated with light output from the light emitting element 101 and reflected by the polarization beam splitter 105 (see FIG. 11A). The light from the object becomes incident on the polarization beam splitter 105, and the light passing through the polarization beam splitter 105 is received by the photodetector 102 (see FIG. 11B). In this example, the light incident on the object and the light from the object are allowed to travel in the same optical path. Therefore, as an example, a condenser lens 106 with a large numerical aperture (NA) can be installed near the object, as illustrated in FIG. 12, so that the amount of light received by the photodetector 102 can be increased. As a result, the detection precision of a moisture content ratio can be further increased.

Optical System for Reference Light

Hereinafter, for convenience, light at wavelengths not absorbed by water is referred to as a "reference light", and light at wavelengths absorbed by water is referred to as a "water-absorbed wavelength light".

The inventors actually manufactured a moisture sensor having an optical system that is the same as the sensor disclosed in Japanese Translation of PCT International Application Publication No. 2008-539422, and measured the moisture content ratio of paper being an object whose moisture content ratio is acquired by another method. There was a large difference between the moisture content ratio thus measured and the moisture content ratio acquired by the other method. In other words, such a moisture sensor was not appropriate for measuring the moisture content ratio of paper.

The inventors then continued earnest investigations, and finally identified a factor causing such a difference from the moisture content ratio acquired by the other method. This factor will now be explained in detail.

Figure 13:
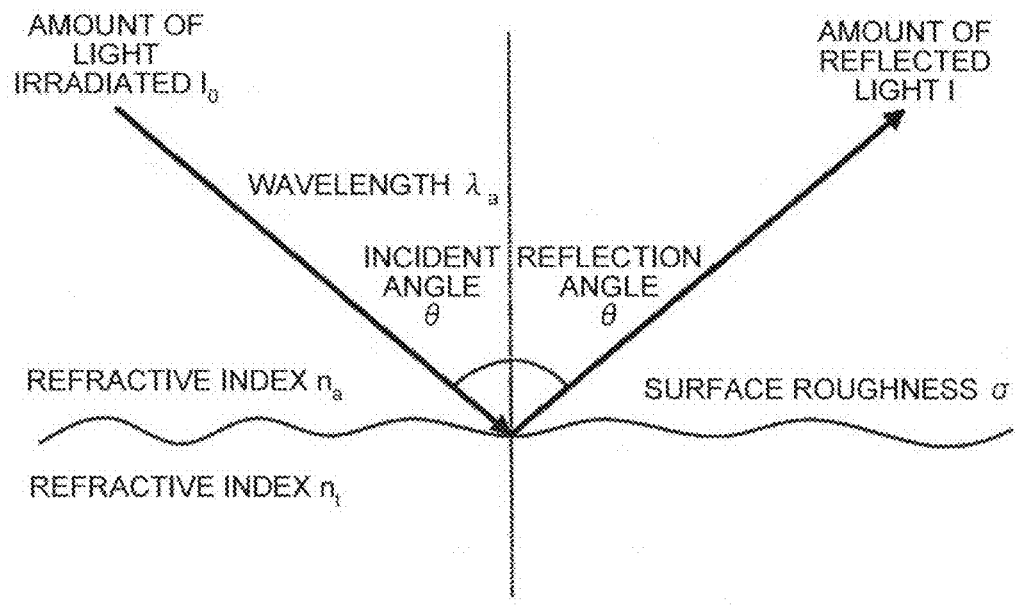
FIG. 13 is a schematic for explaining the intensity of scattered light.

Generally, the intensity of scattered light on a light-scattering member is expressed by Equation (3) below (see FIG. 13). Where, σ is roughness of the surface of the light-scattering member, and $\lambda_a$ is the wavelength of the incident light.

$$\frac{I}{I_0} = \frac{1}{2} \times \left[ \left( \frac{\cos\theta - \sqrt{\left(\frac{n_t}{n_a}\right)^2 - \sin^2\theta}}{\cos\theta + \sqrt{\left(\frac{n_t}{n_a}\right)^2 - \sin^2\theta}} \right)^2 + \left( \frac{\left(\frac{n_t}{n_a}\right)^2 \cos\theta - \sqrt{\left(\frac{n_t}{n_a}\right)^2 - \sin^2\theta}}{\left(\frac{n_t}{n_a}\right)^2 \cos\theta + \sqrt{\left(\frac{n_t}{n_a}\right)^2 - \sin^2\theta}} \right)^2 \right] \times \exp\left[-\left(\frac{4\pi\sigma\cos\theta}{\lambda_a}\right)\right] \quad (3)$$

If the refractive index ($n_t$, $n_a$), the incident angle θ, and roughness of the surface σ are the same, the reference light and the water-absorbed wavelength light will always be detected at the same ratio. If the ratio is constant, a moisture content ratio of various paper types can be calculated highly precisely using the reference light.

Figure 14:
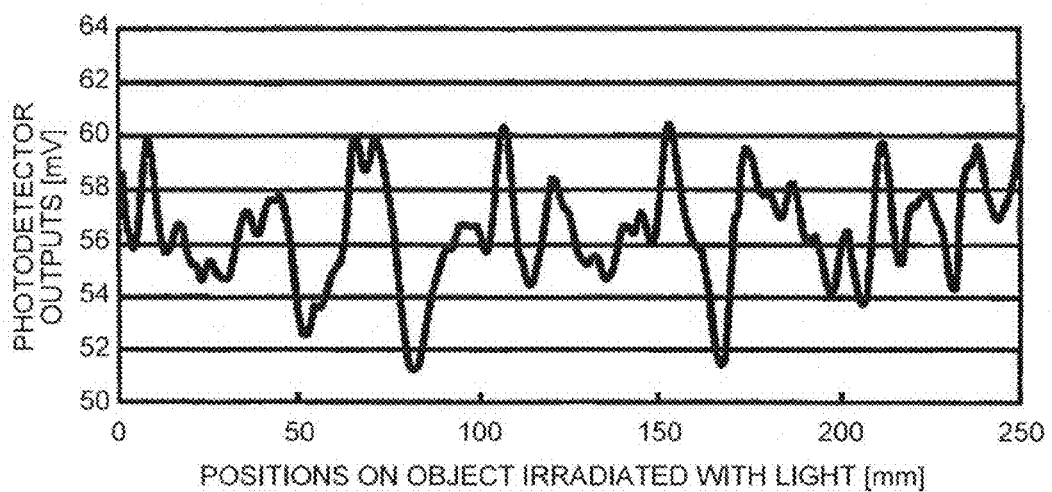
FIG. 14 is a schematic for explaining positions of a object irradiated with light and outputs from a photodetector.

FIG. 14 depicts a relationship between positions on paper irradiated with light and outputs from the photodetector when paper (My Recycle Paper manufactured by Ricoh Company, Ltd.) being the object is irradiated with the reference light. Based on this relationship, it was found out that the photodetector output changed by almost 5 percent when the position irradiated with the light was changed approximately 10 millimeters. The inventors believe that this is caused by an uneven cellulose density distribution. This result also indicates that the refractive index $n_t$ or the roughness of the surface σ in Equation (3) was not even on the surface of the object.

Therefore, it became clear that the area irradiated with the light, the direction irradiated, and the optical path of the irradiation need to be kept almost the same between the reference light and the water-absorbed wavelength light. Furthermore, it was found out that, based on many experiments, in order to detect the moisture content ratio in precision of 1 percent, the area and the direction irradiated, and the optical path of the irradiation need to be matched in order of several-tens of micrometers.

First Exemplary Configuration of Moisture Sensor

Figure 15:
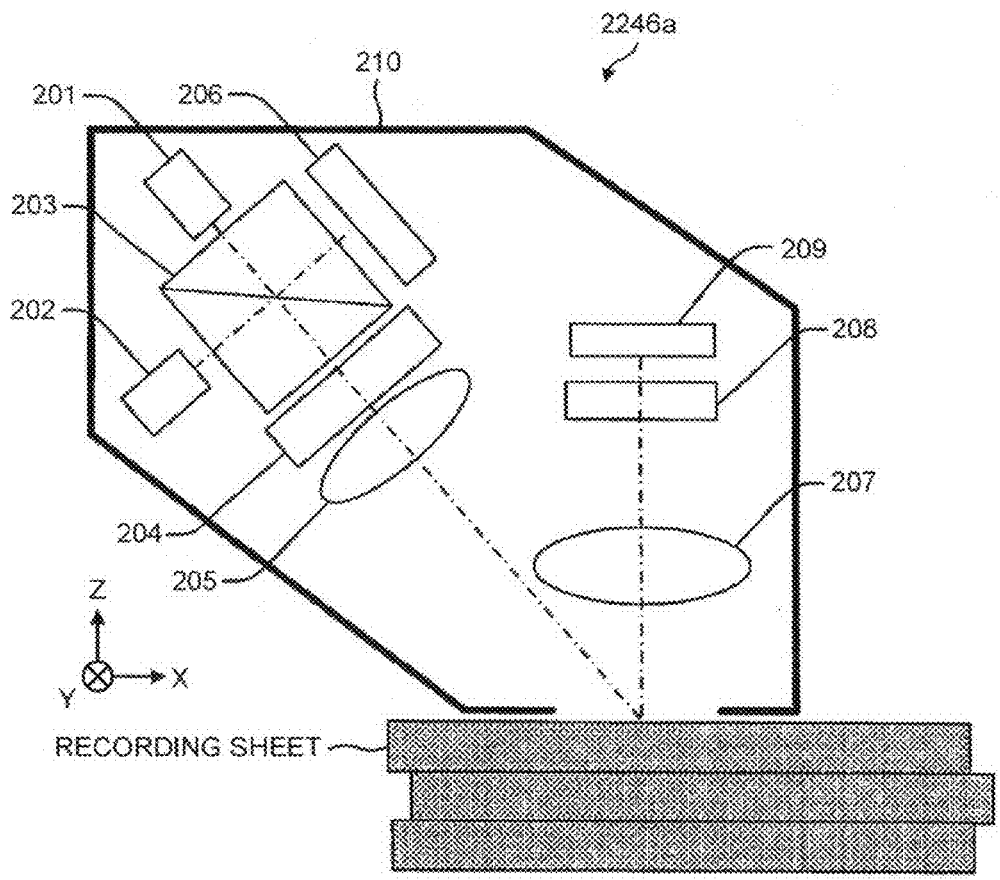
FIG. 15 is a schematic for explaining a first exemplary configuration of a moisture sensor.

FIG. 15 depicts a first exemplary configuration of the moisture sensor (hereinafter referred to as a "moisture sensor 2246a").

The moisture sensor 2246a includes two light emitting diodes (LEDs) (201, 202), a beam splitter 203, two polarizers (204, 208), two condenser lenses (205, 207), two photodiodes (206, 209), and a housing 210 in which these elements are fixed to predetermined positions.

The housing 210 is made of plastic mixed with carbon with a black color, so that generation of ambient light, such as reflected light, is reduced as much as possible. An opening is formed on a surface of the housing 210 brought into contact with the object, and incoming light other than the light from the opening is completely shut out.

The housing 210 is kept in contact with the object. Teflon (registered trademark) coating is applied to the surface of the housing 210 that is kept in contact with the object. This coating is a device for reducing the contact resistance so that the object is prevented from being damaged. The housing 210 is set so that the housing 210 and the object are kept in contact in a stable manner so that the distance between the object and the condenser lens 207 remains constant. In this manner, a detection with a small error is achieved.

The printer controller 2090 supplies a driving current to each of the LEDs. Each of the LEDs is sealed in a transparent resin, and the surface outputting the light has a curved surface. The far-field pattern (FFP) is approximately 10 degrees in full width at half maximum.

The LED 201 outputs light at a wavelength of 1.45 micrometers as the water-absorbed wavelength light. The intensity of the output light is approximately 1 milliwatt.

The LED 202 outputs light at a wavelength of 1.3 micrometers as the reference light. The intensity of the output light is approximately 1 milliwatt.

The beam splitter 203 is disposed in the optical paths of the light output from the LED 201 and the light output from the LED 202. The beam splitter 203 is provided with a half-mirror surface that passes approximately a half of the light output from the LED 201 and a half of the light output from the LED 202 and reflects the remaining of light. A layer of anti-reflection (AR) coating for light at a wavelength of 1.4 micrometers is formed on surfaces of the beam splitter 203 on which the light from the respective LEDs is incident.

The beam splitter 203 is a cube with sides in a length of approximately 5 millimeters. By reducing the size of the beam splitter 203, the length of the optical path from each of the light sources to the condenser lens 205 can be reduced. As a result, the beam diameter of the light incident on the condenser lens 205 can be reduced.

The light output from the LED 201 and passing through the beam splitter 203 and the light output from the LED 202 and reflected by the beam splitter 203 have almost the same path. Therefore, the same area of the object can be irradiated with the water-absorbed wavelength light and with the reference light.

Each of the polarizers is made from a polarizing film pasted on a glass substrate. Each of polarizers has a polarization selection ratio of 99 percent or higher for light at a wavelength of 1.45 micrometers.

The polarizer 204 is disposed in the optical path of the light output from the LED 201 and passing through the beam splitter 203, and the light output from the LED 202 and reflected by the beam splitter 203. The polarizer 204 passes a p-polarized component in each light.

The condenser lens 205 is disposed in the optical path of the light passing through the polarizer 204, and collects the light. The outgoing light from the condenser lens 205 becomes incident on the surface of the object at an incident angle of approximately 45 degrees. A layer of AR coating is formed on the surface of the condenser lens 205. The condenser lens 205 is an aspheric lens with a focal length of approximately 10 millimeters.

A plurality of recording sheets being an object are stacked in the paper feed tray 2060. The light coming out from deep inside of the stacked recording sheets has a polarization direction rotated with respect to the incident light, and is the internally scattered light almost in the Lambert distribution. The internally scattered light is collected by the condenser lens 207.

On the surface of the condenser lens 207, a layer of AR coating is formed. The condenser lens 207 is an aspheric lens with a focal length of approximately 5 millimeters. The aperture of the condenser lens 207 is set to approximately 10 millimeters so as to allow the light to be collected as much as possible. The condenser lens 207 is disposed at a position where no vignetting occurs in light traveling from the condenser lens 205 toward the object.

The polarizer 208 is disposed in the optical path of the light traveled through the condenser lens 207, and passes the light with a polarization direction rotated by 90 degrees with respect to the incident light.

The photodiode 209 receives the light passing through the polarizer 208. A signal output from the photodiode 209 is sent to the printer controller 2090.

The photodiode 206 is disposed in the optical path of the light output from the LED 201 and reflected by the beam splitter 203 and the light output from the LED 202 and passing through the beam splitter 203, and receives each light. A signal output from the photodiode 206 is sent to the printer controller 2090.

The printer controller 2090 controls driving currents for the LED 201 and the LED 202 so that the intensity of light output from the LED 201 and the intensity of the light output from the LED 202 are maintained at predetermined levels based on the signal output from the photodiode 206.

The photodiode 206 is used for monitoring, and receives the light without being collected from the beam splitter 203, because a light intensity somewhat low is acceptable.

Both of these photodiodes are photodiodes using a indium gallium arsenide (InGaAs) based compound material, and has sensitivity to light up to approximately 2.0 micrometer wavelength. The size of the light receiving surface is approximately a diameter of 1 millimeter, and is not provided with a Peltier cooler or the like.

The photodiodes are implemented in a metallic can package. A current applied with a photoelectric conversion is amplified by approximately $10^7$ times by an operational amplifier, and output as a voltage.

In the moisture sensor 2246a, the p-polarized light and the s-polarized light may be switched.

Using the moisture sensor 2246a, the photodiode 209 is enabled to receive the light scattered deep inside of the recording sheet, and having a long optical path length inside of the recording sheet in a selective manner. In other words, the moisture sensor 2246a is a moisture sensor with high detection sensitivity.

The inventors actually measured the moisture content ratio of standard paper in a thickness of approximately 100 micrometers and a smoothness of approximately 100 seconds using the moisture sensor 2246a. The moisture content ratio of this standard paper is known to change from 5.2 percent to 8.3 percent, through so-called loss-on-drying experiments in which the moisture content ratio is acquired based on a change in the weight before and after drying, while humidity is changed from 40 percent to 70 percent. Despite the inventors conducted experiments under various humidity conditions without limiting to the range mentioned above, an example in which the humidity was changed from 40 percent to 70 percent will be explained as an example hereunder.

Under such a humidity change, the amount of the internally scattered light did not change for the reference light output from the LED 202. By contrast, the amount of internally scattered light indicated a change of 2.5 percent for the water-absorbed wavelength light output from the LED 201. Because a change in the moisture content ratio is 3.1 percent (=8.3 percent−5.2 percent) when the humidity is changed from 40 percent to 70 percent, it can be concluded that 0.8 percent (=2.5 percent÷3.1 percent) change in the amount of internally scattered light corresponds to a change of one percent in a moisture content ratio.

Comparative Example

As a comparative example of the moisture sensor 2246a, the inventors manufactured the moisture sensor 2246a with the two polarizers removed, and measured the moisture content ratio of the same standard paper. In this example, under the condition that the humidity was changed from 40 percent to 70 percent and the moisture content ratio of the paper was changed from 5.2 percent to 8.3 percent, a change in the amount of internally scattered light was 1.0 percent for the water-absorbed wavelength light output from the LED 201. In this case, it can be concluded that a change of 0.32 percent (=1.0 percent÷3.1 percent) in the amount of internally scattered light corresponds to a change of one percent in the moisture content ratio. This change was approximately one third of the measurement result acquired by the moisture sensor 2246a. This change is so small that the signal could become buried in noise. Therefore, the measurement precision is low.

Second Exemplary Configuration of Moisture Sensor

Figure 16:
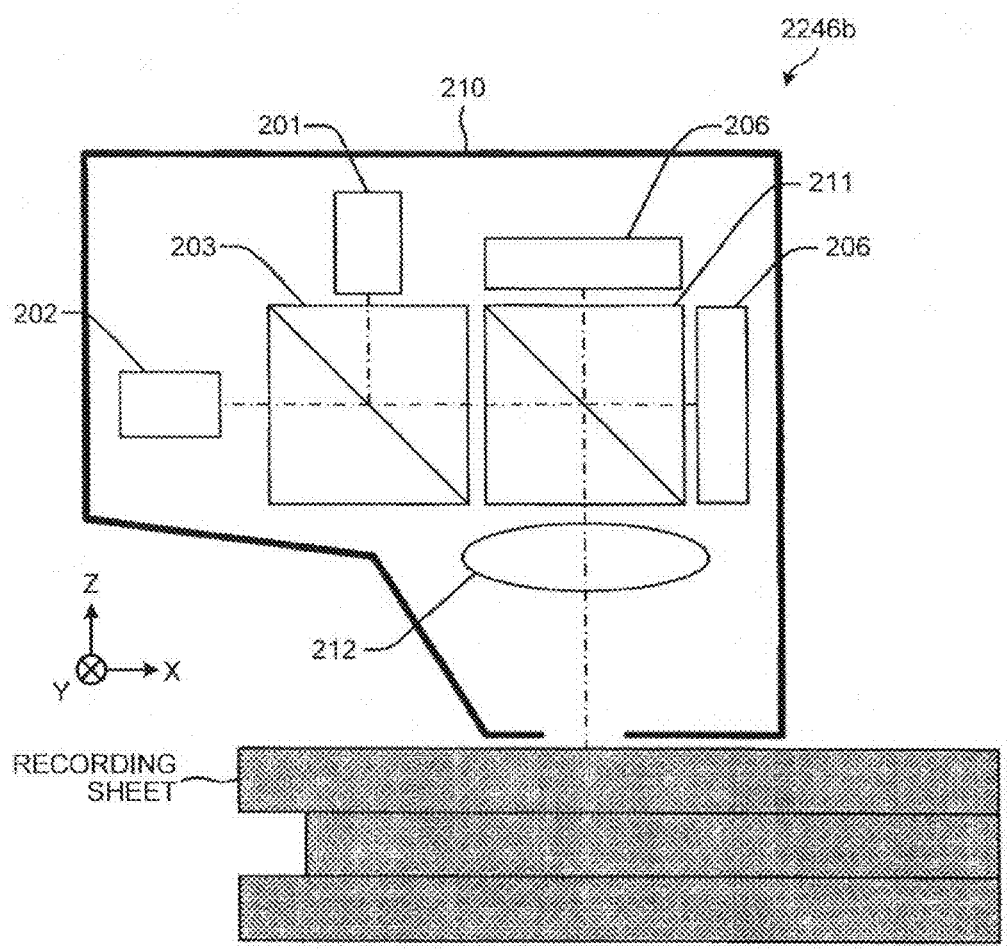
FIG. 16 is a schematic for explaining a second exemplary configuration of the moisture sensor.

FIG. 16 depicts a second exemplary configuration of the moisture sensor (hereinafter referred to as a "moisture sensor 2246b"). The moisture sensor 2246b is characterized in that the size of the optical system is made smaller than that in the moisture sensor 2246a. Mainly explained hereunder are differences from the moisture sensor 2246a, and the same reference numerals are assigned to elements that are the same or equivalent to those included in the moisture sensor 2246a, and explanations thereof are simplified or omitted hereunder.

The moisture sensor 2246b includes the two LEDs (201, 202), the beam splitter 203, a polarization beam splitter 211, a condenser lens 212, the two photodiode (206, 209), and the housing 210 in which these elements are fixed to predetermined positions.

The polarization beam splitter 211 is disposed in the optical path of the light output from the LED 201 and reflected by the beam splitter 203, and the light output from the LED 202 and passing through the beam splitter 203. The polarization beam splitter 211 has a polarizing reflecting surface that passes a p-polarized component and reflects an s-polarized component included in each light.

The polarization beam splitter 211 has a polarization selectivity of 99 percent or higher. The polarization beam splitter 211 is a cube with sides in a length of approximately 5 millimeters.

The water-absorbed wavelength light and the reference light that are output from the beam splitter 203 and reflected by the polarization beam splitter 211 have almost the same path. Therefore, the same area of the object can be irradiated with the water-absorbed wavelength light and with the reference light.

Alternatively, a reflecting polarization splitting element using a wire grid, for example, may be used instead of the polarization beam splitter 211.

A light-blocking layer is formed on the surfaces of the beam splitter 203, excluding the surface on which the light from each of the LEDs is incident, and excluding an outgoing surface from which the light travels toward the polarization beam splitter 211, so that the light is not let out except through the outgoing surface.

The condenser lens 212 is disposed in the optical path of the light output from the beam splitter 203 and reflected by the polarization beam splitter 211, and collects the light. The light output from the condenser lens 212 becomes incident on the surface of the object at an incident angle of approximately 0 degrees. A layer of AR coating is formed on the surface of the condenser lens 212. The condenser lens 212 is an aspheric lens with a focal length of approximately 5 millimeters.

The position of the condenser lens 212 is adjusted so that the focal point thereof comes near the surface of the object.

The light from the object and incident on the condenser lens 212 becomes incident on the polarization beam splitter 211.

The photodiode 209 receives the light reflected on the object through the condenser lens 212 and the polarization beam splitter 211.

The photodiode 206 is disposed in the optical path of the light output from the beam splitter 203 toward the polarization beam splitter 211 and passing through the polarization beam splitter 211.

Third Exemplary Configuration of Moisture Sensor

Figure 17:
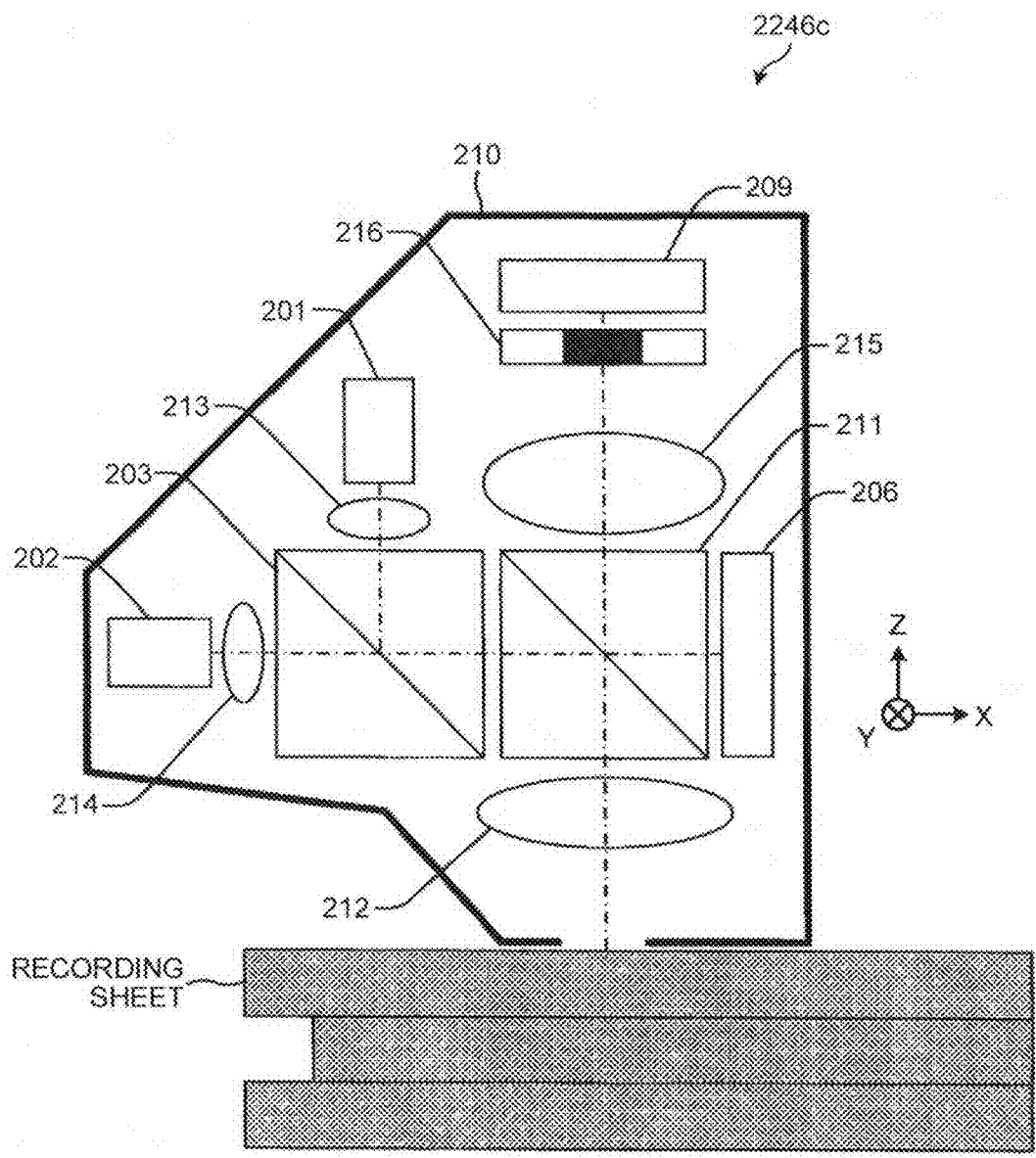
FIG. 17 is a schematic for explaining a third exemplary configuration of the moisture sensor.
Figure 18:
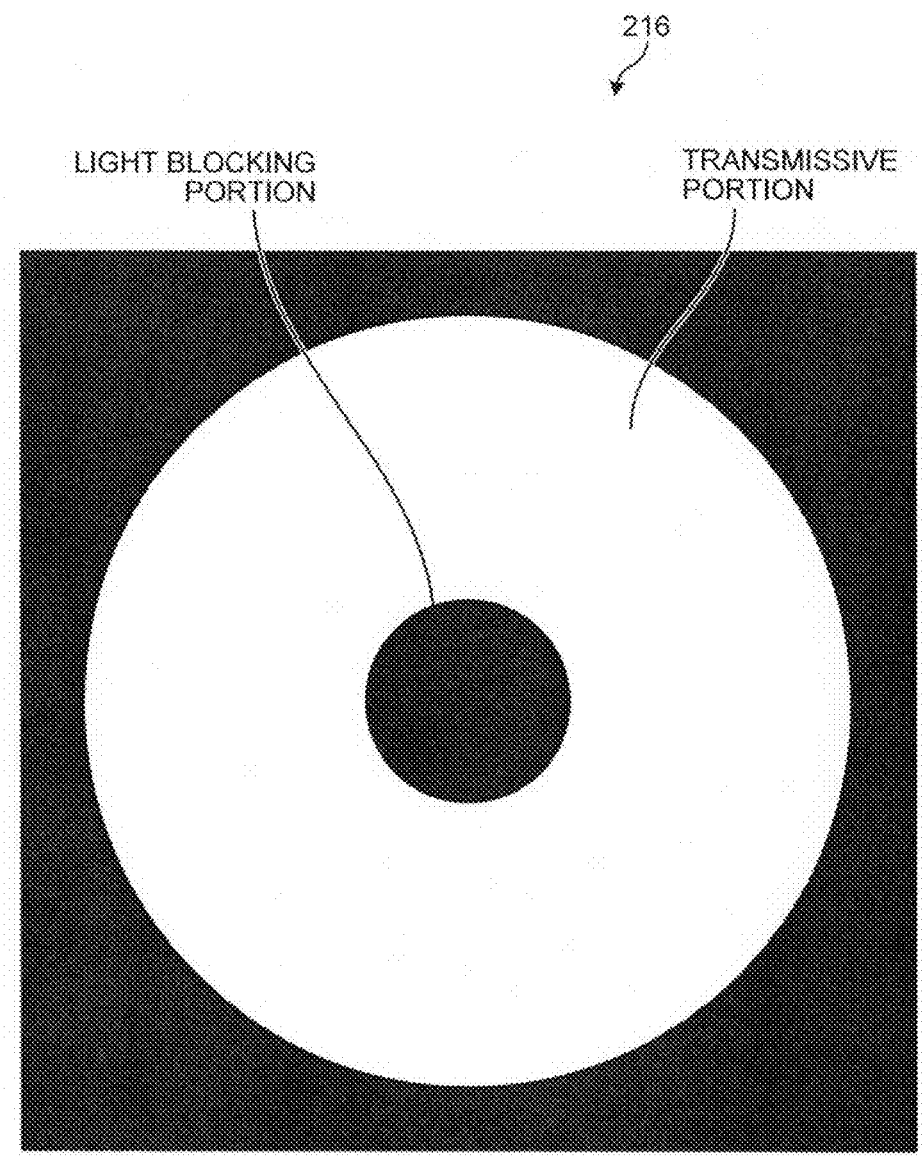
FIG. 18 is a schematic for explaining a douser.

FIG. 17 depicts a third exemplary configuration of the moisture sensor (hereinafter referred to as a "moisture sensor 2246c"). The moisture sensor 2246c has a configuration in which a lens and a douser are added to the moisture sensor 2246b. Mainly explained hereunder are differences from the moisture sensor 2246b, and the same reference numerals are assigned to elements that are the same or equivalent to those included in the moisture sensor 2246a and the moisture sensor 2246b and explanations thereof are simplified or omitted hereunder.

The moisture sensor 2246c includes the two LEDs (201, 202), the beam splitter 203, the polarization beam splitter 211, the two photodiodes (206, 209), two condenser lenses (212, 215), two collimator lenses (213, 214), a douser 216, and the housing 210 in which these elements are fixed to predetermined positions.

The collimator lens 213 is positioned between the LED 201 and the beam splitter 203, and collimates the light output from the LED 201.

The collimator lens 214 is positioned between the LED 202 and the beam splitter 203, and collimates the light output from the LED 202.

The condenser lens 212 is a lens having a shape similar to that of an objective lens of a microscope, and has an NA of approximately 0.5, and magnification of approximately 10 times. The working distance (WD) is set to approximately 1 millimeter, and the aperture of the lens is 5 millimeters. This configuration realizes a bright optical system enabled to receive a large amount of scattered light, because the NA is much larger than that in the moisture sensor 2246b.

The position of the condenser lens 212 is adjusted so that the focal point thereof comes near the surface of the object.

The condenser lens 215 is disposed in the optical path of the light reflected by the object and passing through the condenser lens 212 and the polarization beam splitter 211, and collects the light.

The condenser lens 212 and the condenser lens 215 form a confocal optical system. Therefore, the same lens as the condenser lens 212 may be used for the condenser lens 215.

The douser 216 is positioned between the condenser lens 215 and the photodiode 209. The douser 216 has a light blocking portion at a focal point on a +Z side of the confocal optical system. A black, light absorbing film, in a diameter of approximately 100 micrometers, is provided to the light blocking portion (see FIG. 18).

The photodiode 209 receives the light passing through a transmissive portion surrounding the light blocking portion of the douser 216.

Although polarization splitting achieved by the polarization beam splitter 211 is used to suppress the photodiode 209 from receiving light reflected near the surface of the object, an effect achieved by the polarization splitting is not sufficient when the object is a type of paper with a surface having a smoothness exceeding 1000 seconds, such as coated paper.

To allow such a type of paper with a surface smoothness exceeding 1000 seconds to be used as an object, in the moisture sensor 2246c, the confocal optical system is used as an optical system for selectively removing light reflected near the surface of the object. In this configuration, the light reflected near the surface of the object is collected near the light blocking portion of the douser 216 by the condenser lens 215, and blocked by the light blocking portion. Therefore, the photodiode 209 does not receive the light reflected near the surface of the object.

By contrast, because the light scattered inside of the object is light that does not pass through the focal point of the confocal optical system, the light passes through the transmissive portion of the douser. In other words, the photodiode 209 receives the light scattered inside of the object.

Because the light incident on the beam splitter 203 and the light incident on the polarization beam splitter 211 are collimated, multi-reflection might occur between parallel planes such as the surface of each of the LEDs, the side surface of the beam splitter 203, and the side surface of the polarization beam splitter 211. When the multi-reflected light has some effects on the outputs from the respective photodiodes, it is preferable to incline the beam splitter 203 and the polarization beam splitter 211 slightly with respect to a plane perpendicular to the collimated light. Alternatively, a $\lambda/4$ plate may be inserted between collimator lens and the beam splitter 203.

Furthermore, in the moisture sensor 2246c, because light beams output from the LEDs are collimated with the respective collimator lenses, light utilization can be improved.

Modification

Figure 19:
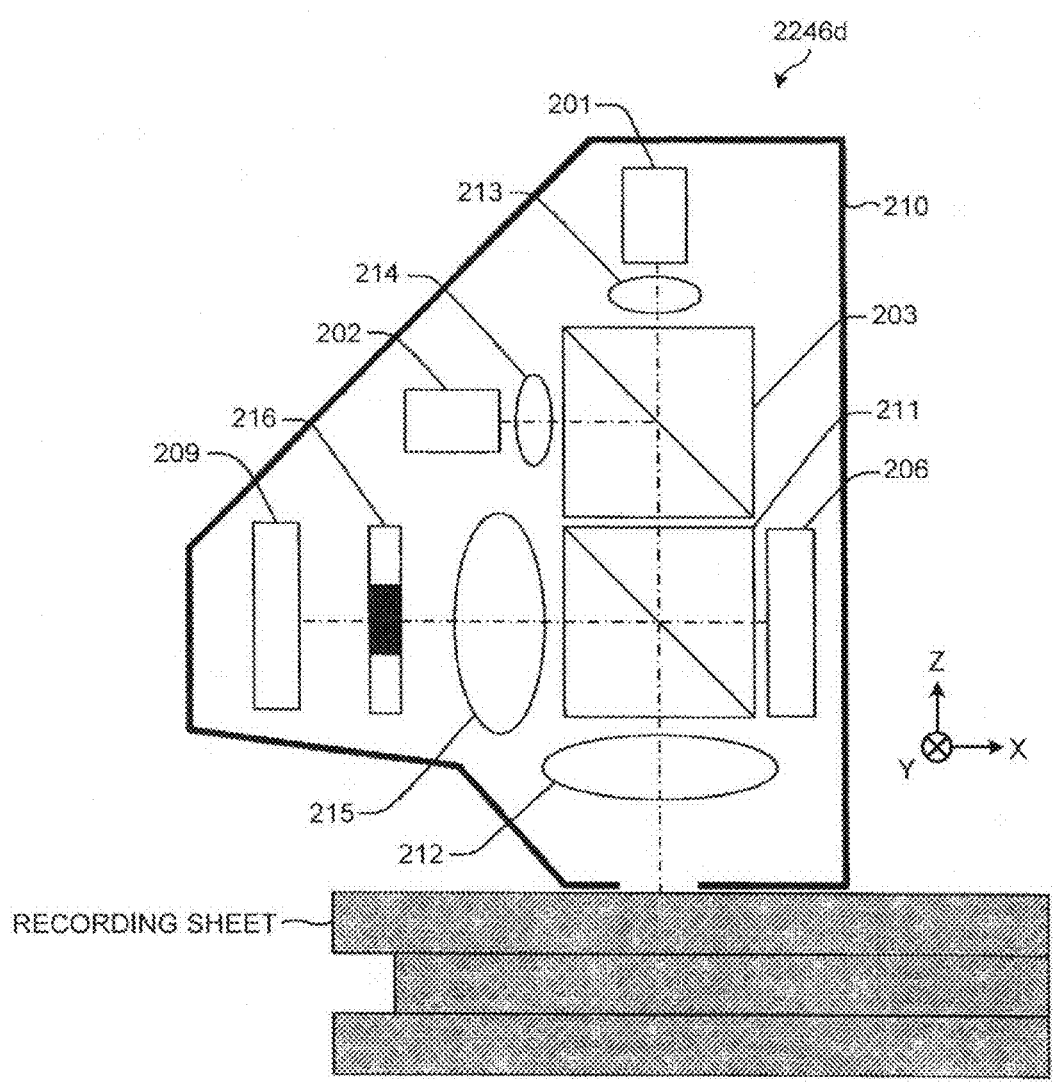
FIG. 19 is a schematic for explaining a modification of the third exemplary configuration of the moisture sensor.

FIG. 19 depicts a modification of the moisture sensor 2246c (hereinafter referred to as a "moisture sensor 2246d").

The moisture sensor 2246d is characterized in that the object is irradiated with light passing through the polarization beam splitter 211.

Figure 20:
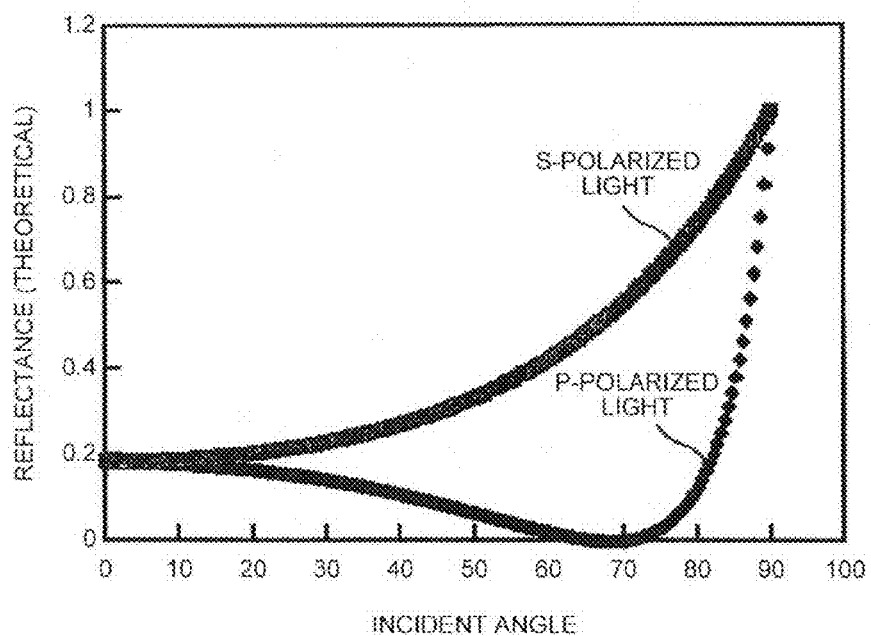
FIG. 20 is a schematic for explaining a relationship between incident angles and reflectance in p-polarized light and s-polarized light.

FIG. 20 illustrates a relationship between an incident angle and reflectance of p-polarized light and s-polarized light, acquired from the Fresnel equation. This relationship indicates that, when the incident angle is increased within a range between 0 degrees to approximately 70 degrees, the reflectance decreased for p-polarized light, and the reflectance increases for s-polarized light. In other words, when the incident angle is increased, the transmittance increases for p-polarized light, and the transmittance decreases for s-polarized light. Therefore, the amount of light penetrating inside of the recording sheet can be increased by using p-polarized light as light incident on the recording sheet, and making the incident angle as large as possible within the range between 0 degrees to approximately 70 degrees in the moisture sensor 2246a. As a result, the amount of internally scattered light received by the photodiode 206 can be increased. In this manner, the detection precision can be improved.

The paper-type determining sensor 2245 will now be explained.

Figure 21:
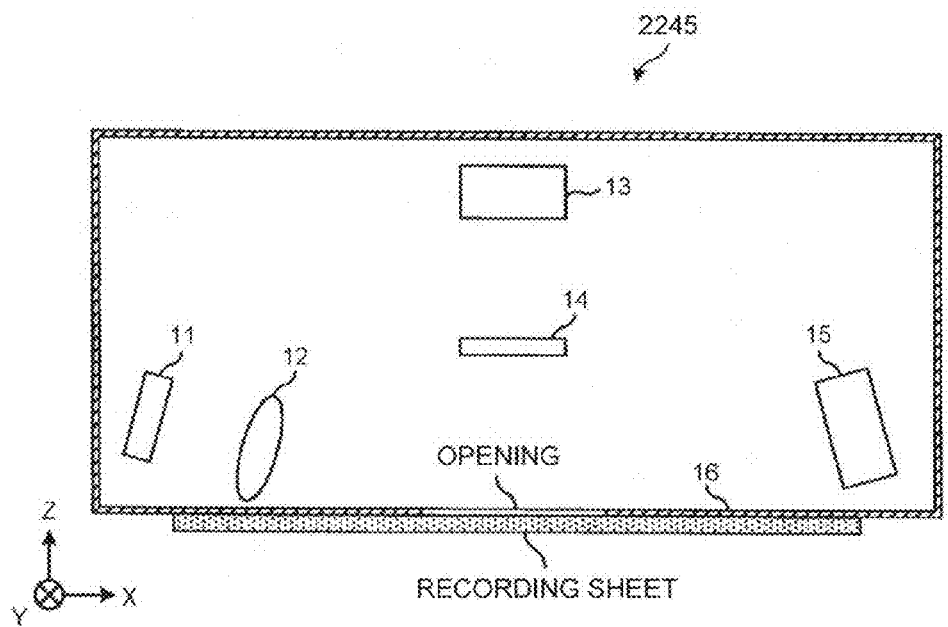
FIG. 21 is a schematic for explaining a paper-type determining sensor.

As illustrated in FIG. 21, the paper-type determining sensor 2245 includes, as an example, a light source 11, a collimator lens 12, two photoreceptors (13, 15), a polarization filter 14, and a dark box 16 in which these elements are housed.

The dark box 16 is a box member made of a metal, e.g., aluminum, and applied with a black alumite treatment so as to reduce the effects of ambient light and stray light.

Figure 22:
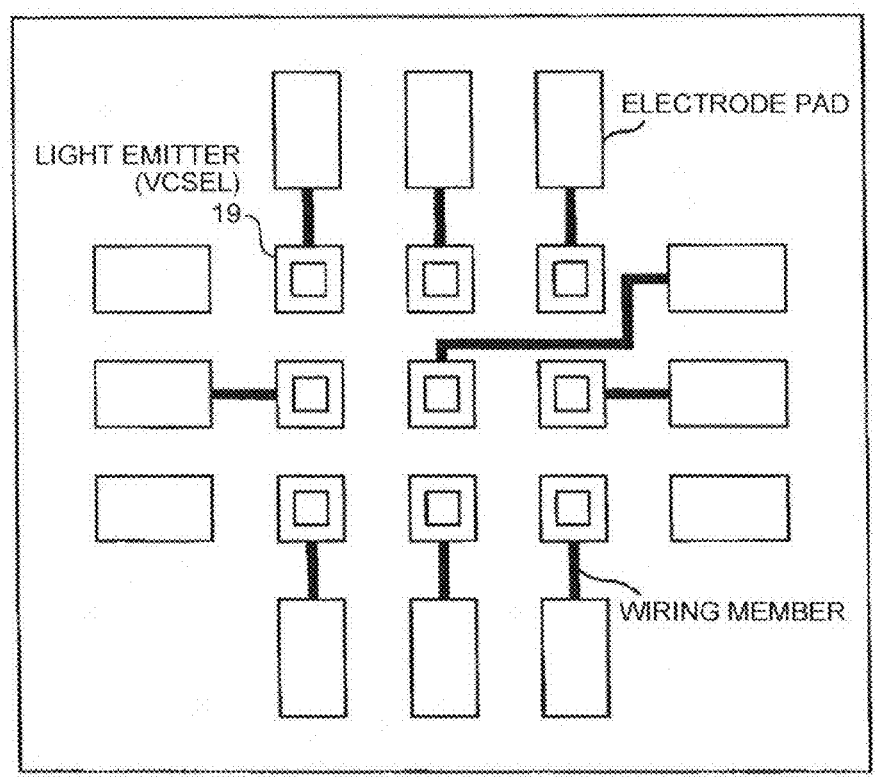
FIG. 22 is a schematic for explaining a vertical-cavity surface-emitting laser (VCSEL) array.

The light source 11 includes a plurality of light-emitting elements. Each of the light-emitting elements is a vertical-cavity surface-emitting laser (VCSEL) formed on a common substrate. In other words, the light source 11 includes a VCSEL array. In this configuration, as an example, nine light-emitting elements 19 are arranged two-dimensionally, as illustrated in FIG. 22.

Figure 23:
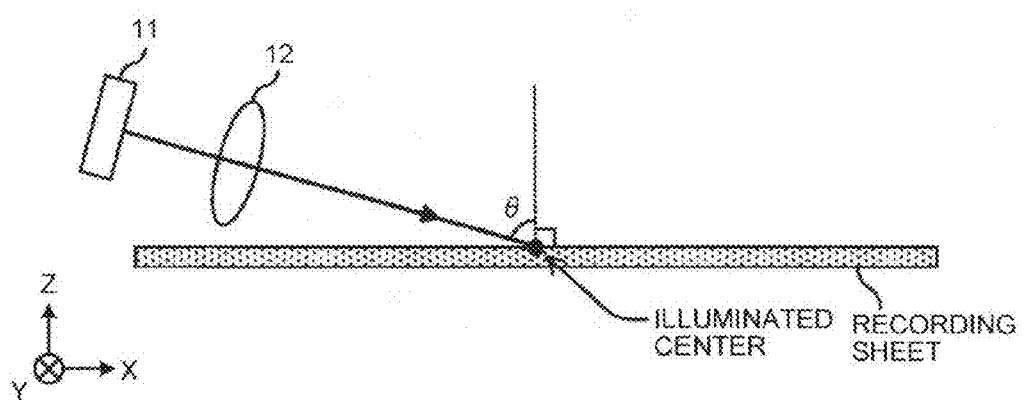
FIG. 23 is a schematic for explaining an incident angle of light incident on a recording sheet.

The light source 11 is positioned so as to allow the recording sheet to be irradiated with s-polarized light. The incident angle θ of the light beam from the light source 11 on the recording sheet (see FIG. 23) is 80 degrees. In FIG. 23, to facilitate easier understanding, the dark box 16 is not illustrated.

The collimator lens 12 is disposed in the optical path of the light beam output from the light source 11, and collimates the light beam. The light beam passing through the collimator lens 12 passes through an opening formed on the dark box 16, and illuminates the recording sheet. Hereinafter, the center of the area of the recording sheet surface illuminated by the light beam is simply referred to as an "illuminated center". The light beam passing through the collimator lens 12 is referred to as "irradiation light".

The polarization filter 14 is positioned on the +Z side of the illuminated center. The polarization filter 14 is a polarization filter that passes p-polarized light and blocks s-polarized light. Alternatively, a polarization beam splitter having a function equivalent to that of the polarization filter 14 may be used in replacement of the polarization filter 14.

Figure 24:
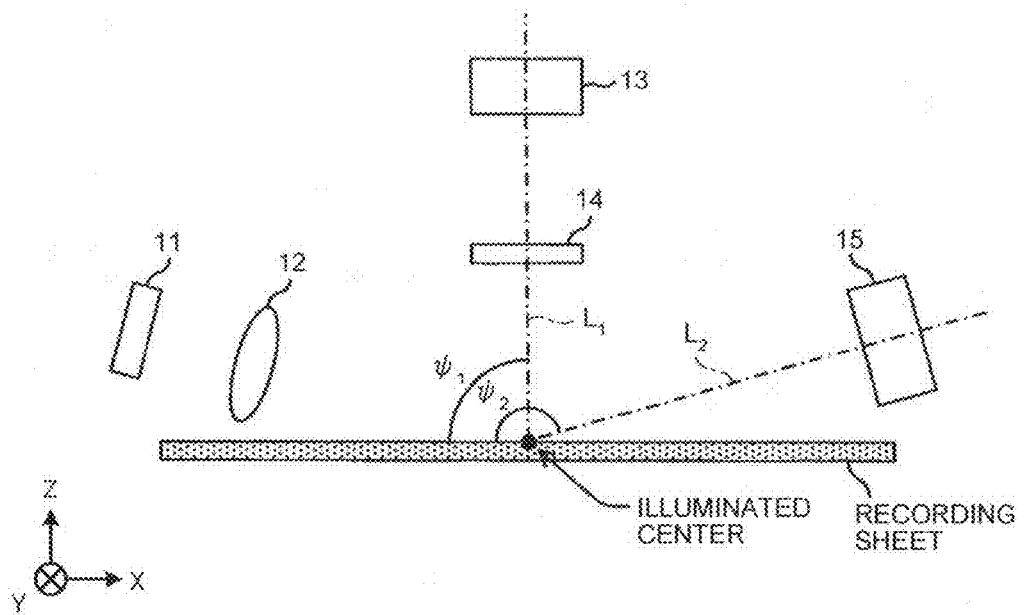
FIG. 24 is a schematic for explaining where two photoreceptors are positioned.

The photoreceptor 13 is positioned on the +Z side of the polarization filter 14. In this configuration, as illustrated in FIG. 24, an angle $\psi_1$ formed by a line $L_1$ connecting the illuminated center, the center of the polarization filter 14, and the center of the photoreceptor 13, and the surface of the recording sheet is 90 degrees.

The photoreceptor 15 is positioned on a +X side of the illuminated center in an X axis direction. An angle $\psi_2$ formed by a line $L_2$ connecting the illuminated center and the center of the photoreceptor 15, and the surface of the recording sheet is 170 degrees.

The center of the light source 11, the illuminated center, the center of the polarization filter 14, the center of the photoreceptor 13, the center of the photoreceptor 15 are positioned on an almost the same plane.

The light reflected by the recording sheet when the recording sheet is illuminated can be classified into reflected light that is reflected on the surface of the recording sheet and reflected light that is reflected internally in the recording sheet. The reflected light that is reflected on the surface of the recording sheet can be further classified into reflected light that is specular-reflected light (hereinafter referred to as "surface specular-reflected light", for convenience) and surface scattered light (see FIGS. 25A and 25B).

The surface of a recording sheet has parts with a flat surface and parts with an inclined surface, and the ratio between these parts determines the smoothness of the surface of a recording sheet. The light reflected by a part with a flat surface becomes surface specular-reflected light, and the light reflected by a part with a slanted surface becomes surface scattered light. The surface scattered light is a completely scatter-reflected light, and the directions of the reflections can be considered to have an isotropic nature. When the smoothness is higher, the amount of surface specular-reflected light increases.

Figure 25A:
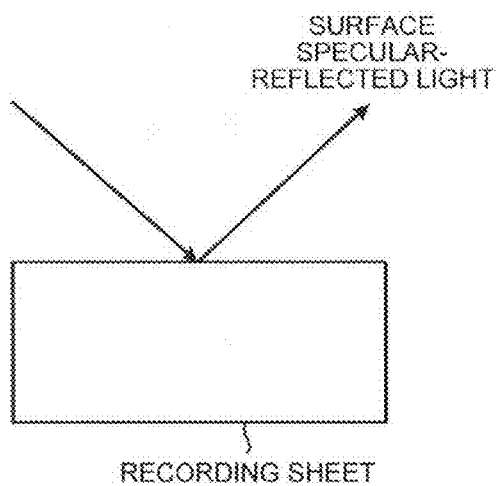
FIG. 25A is a schematic for explaining surface specular-reflected light.
Figure 25B:
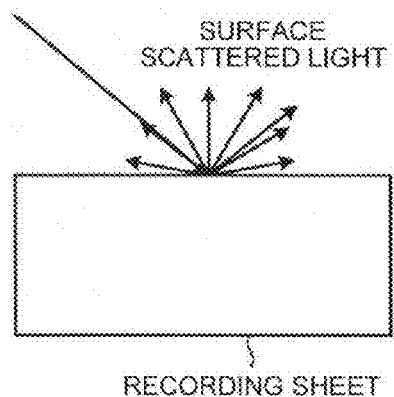
FIG. 25B is a schematic for explaining surface scattered light.
Figure 25C:
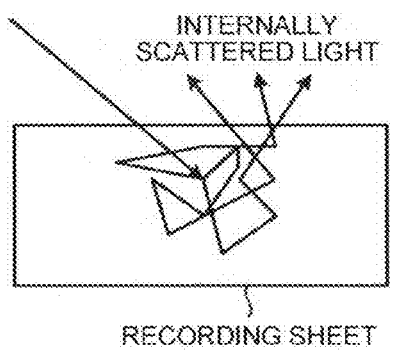
FIG. 25C is a schematic for explaining internally scattered light.
Figure 26:
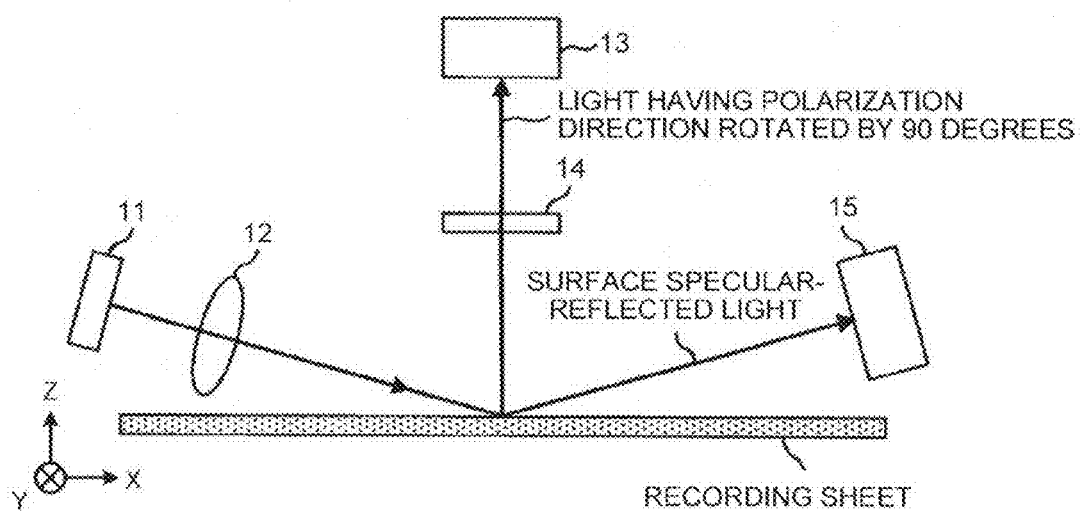
FIG. 26 is a schematic for explaining light received by each of the photoreceptors.

By contrast, the reflected light from inside of the recording sheet consists only of the internally scattered light, because, when the recording sheet is a general printing paper, a light multiple-scatters among the fibers of the paper (see FIG. 25C). The internally scattered light is also a completely scatter-reflected light, and, therefore, the directions in which the light is reflected can be considered to have an isotropic nature.

The polarization direction of the surface specular-reflected light and the polarization direction of the surface scattered light are the same as that of the incident light. For the polarization direction to be rotated on the surface of the recording sheet, the incident light needs to be reflected on a plane that is oblique along the direction of the rotation with respect to the axis of the incident light. In this example, because the center of the light source, the illuminated center, and the center of each of photoreceptors are on the same plane, reflected light having a polarization direction rotated on the surface of the recording sheet is not reflected toward the photoreceptors.

By contrast, the polarization direction of the internally scattered light is rotated with respect to the polarization direction of the incident light. The inventors believe that the polarization direction is rotated because the light is rotated as the light passes through the fibers and becomes multiple-scattered.

Therefore, both of the surface scattered light and the internally scattered light become incident on the polarization filter 14. Because the polarization direction of the surface scattered light is the same as that of the incident light, the surface scattered light is blocked by the polarization filter 14. By contrast, because the polarization direction of the internally scattered light is rotated with respect to the polarization direction of the incident light, the internally scattered light has some light having a polarization rotated by 90 degrees. The light rotated by 90 degrees in the internally scattered light passes through the polarization filter 14, and received by the photoreceptor 13 (see FIG. 26).

It has been confirmed by the inventors that the amount of light rotated by 90 degrees in the internally scattered light is highly correlated with the thickness and the density of the recording sheet. This is because the amount of light rotated by 90 degrees is dependent on the length of the path taken by the light penetrated into the fibers of the recording sheet.

A very small part of the surface specular-reflected light, the surface scattered light, and the internally scattered light becomes incident on the photoreceptor 15. In other words, mainly incident on the photoreceptor 15 is the surface specular-reflected light.

Each of the photoreceptor 13 and the photoreceptor 15 outputs an electrical signal (a photoelectric-converted signal) corresponding to the amount of light received by each of these photoreceptors to the printer controller 2090. Hereinafter, a level of the signal output from the photoreceptor 13 when recording sheet is irradiated with the light beam output from the light source 11 is referred to as $S_1$, and a level of the signal output from the photoreceptor 15 is referred to as $S_2$.

In this embodiment, $S_1$ and $S_2$ are measured in a pre-shipment process such as an adjustment process for a recording sheet of each of a plurality of brands of recording sheets that are usable in the color printer 2000, and the measurement results are stored in the ROM in the printer controller 2090 as a "recording sheet determination table" in advance.

In addition, for a recording sheet of each of the brands of recording sheets that are usable in the color printer 2000, development conditions and transfer conditions most appropriate for a moisture content ratio in the respective stations are determined in a pre-shipment process such as an adjustment process, and the determination results are stored in the ROM in the printer controller 2090 as a "development and transfer table" in advance.

Figure 27:
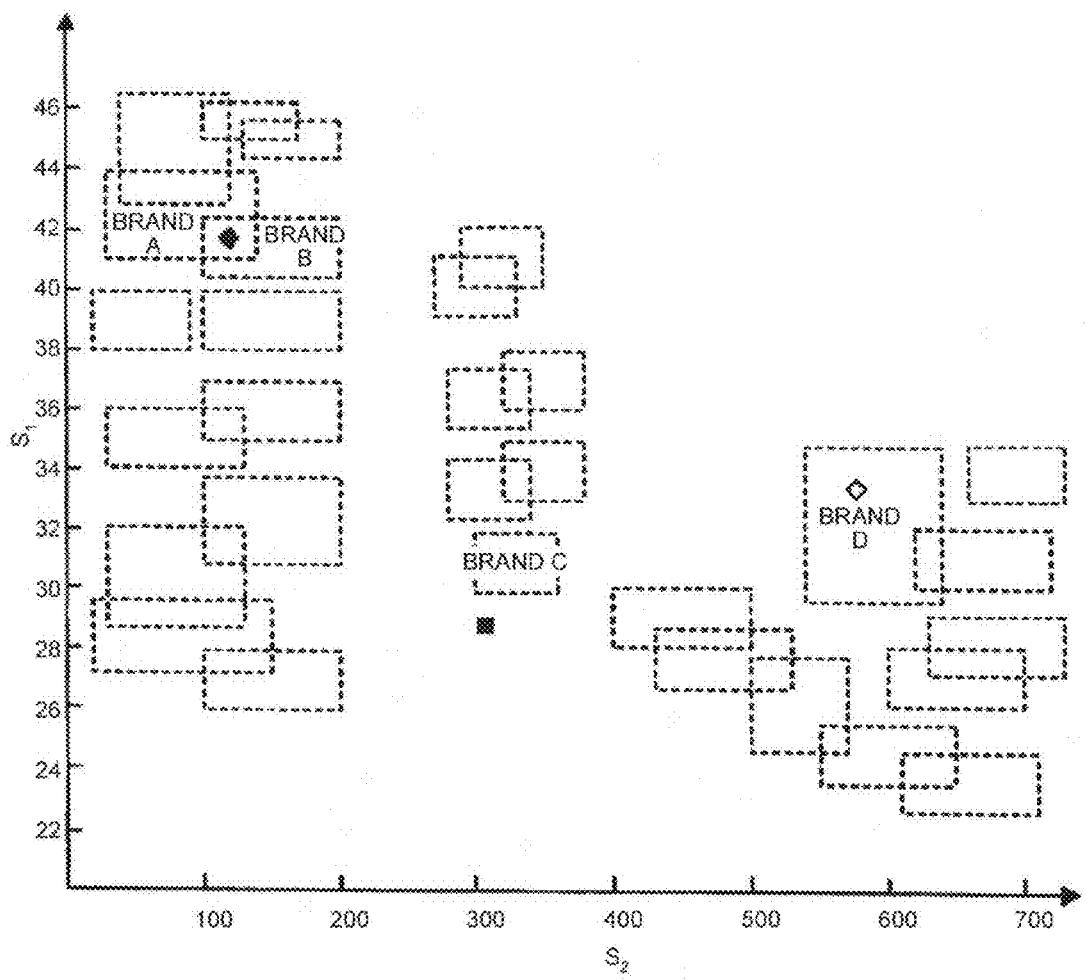
FIG. 27 is a schematic for explaining a relationship between S1, S2, and a brand of recording sheets.
Figure 28:
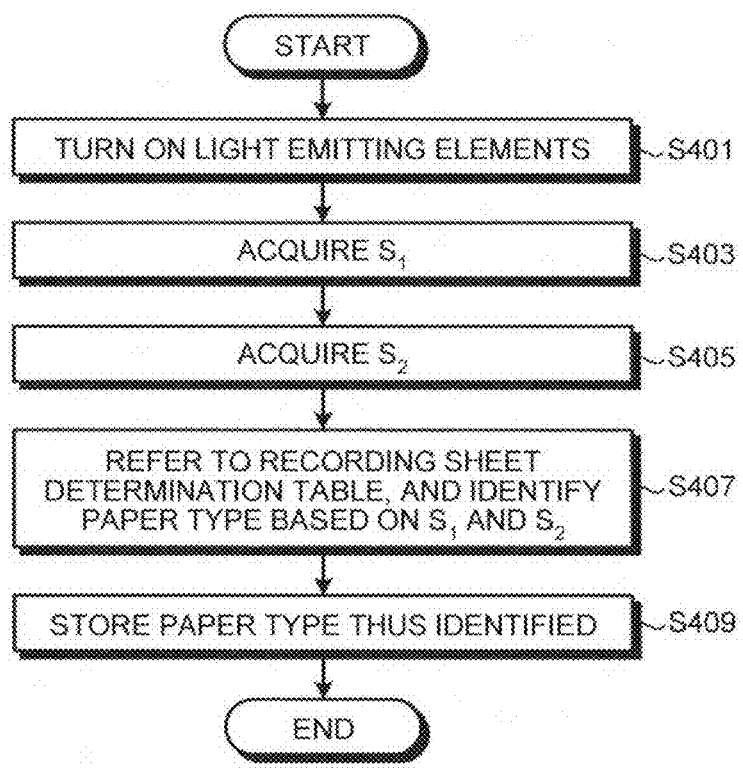
FIG. 28 is a flowchart for explaining a paper-type determining process.
Figure 29:
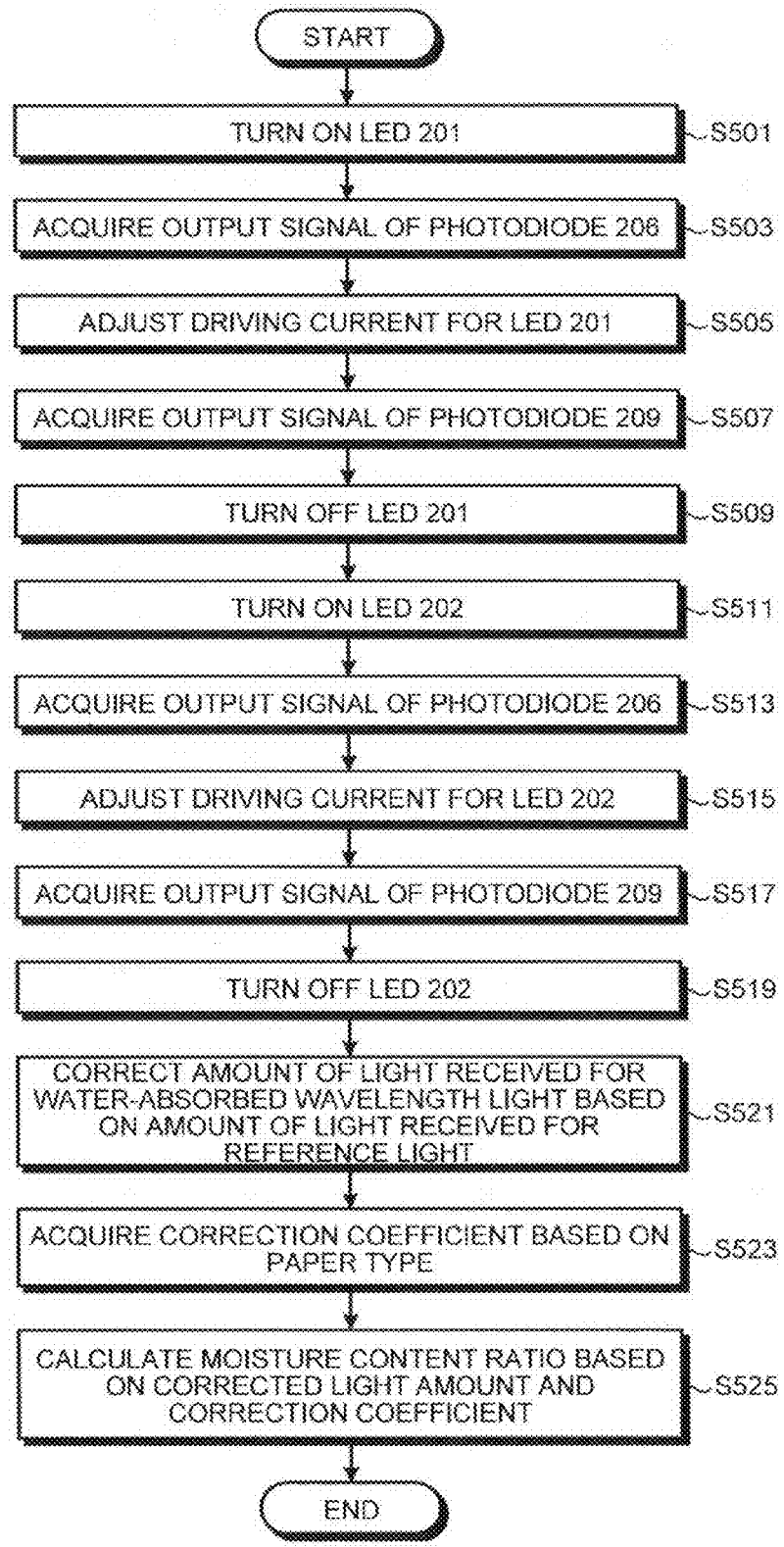
FIG. 29 is a flowchart for explaining a moisture content ratio detecting process.

FIG. 27 illustrates measurements of S1 and S2 acquired from recording sheets of 30 different brands sold domestically. A frame illustrated in FIG. 27 indicates a range of fluctuations among the same brand. For example, when the measurements $S_1$ and $S_2$ are plotted by the symbol of white diamond in FIG. 27, the recording sheet is identified as a brand D. When the measurements $S_1$ and $S_2$ are plotted by the symbol of black square in FIG. 27, the recording sheet is identified as a brand C that is located nearest. When the measurements S1 and S2 are plotted by the symbol of black diamond in FIG. 27, the recording sheet is either a brand A or a brand B. In such a case, a difference between the average in the brand A and this measurement is calculated, and a difference between the average in the brand B and this measurement is calculated as well. The recording sheet is then identified as a recording sheet of the brand with a smaller difference, for example. Alternatively, the fluctuation may be recalculated assuming that the recording sheet is the brand A, the fluctuation may be recalculated assuming that the recording sheet is the brand B, and a brand with the smaller fluctuation may be selected.

The printer controller 2090 performs a paper-type determining process of a recording sheet using the paper-type determining sensor 2245 when the color printer 2000 is powered on, and when the recording sheets are supplied to the paper feed tray 2060, for example. The paper-type determining process performed by the printer controller 2090 will now be explained with reference to FIG. 28. The flowchart illustrated in FIG. 28 corresponds to a sequence in a processing algorithm executed by the printer controller 2090 in the paper-type determining process.

At Step S401 that is the first step, the printer controller 2090 turns on a plurality of light-emitting elements in the paper-type determining sensor 2245 simultaneously.

At Step S403 following next, the printer controller 2090 acquires $S_1$ from an output signal of the photoreceptor 13.

At Step S405 following next, the printer controller 2090 acquires $S_2$ from an output signal of the photoreceptor 15.

At Step S407 following next, the printer controller 2090 refers to the recording sheet determination table, and identifies the brand of the recording sheet based on $S_1$ and $S_2$ thus acquired.

At Step S409 following next, the printer controller 2090 stores the brand of the recording sheet thus identified in the RAM, and ends the paper-type determining process.

When the printer controller 2090 receives a print job request from a user, the printer controller 2090 performs a moisture content ratio detecting process for the recording sheet using the moisture sensor 2246. The moisture content ratio detecting process performed by the printer controller 2090 will now be explained with reference to FIG. 29. The flowchart illustrated in FIG. 29 corresponds to a sequence in a processing algorithm executed by the printer controller 2090 in the moisture content ratio detecting process.

At Step S501 that is the first step, the printer controller 2090 turns on the LED 201.

At Step S503 following next, the printer controller 2090 acquires an output signal of the photodiode 206, and acquires the amount of light output from the LED 201.

At Step S505 following next, based on the amount of light output from the LED 201 thus acquired, the printer controller 2090 adjusts a driving current supplied to the LED 201 so as to maintain the amount of light output from the LED 201 at a predetermined level.

At Step S507 following next, the printer controller 2090 acquires an output signal of the photodiode 209, and acquires the amount of light received by the photodiode 209. Hereinafter, the amount of received light thus acquired is referred to as an "amount of light received for the water-absorbed wavelength light", for convenience.

At Step S509 following next, the LED 201 is turned off.
At Step S511 following next, the LED 202 is turned on.

At Step S513 following next, the printer controller 2090 acquires an output signal of the photodiode 206, and acquires the light amount of light output from the LED 202.

At Step S515 following next, based on the amount of light output from the LED 202 thus acquired, the printer controller 2090 adjusts a driving current supplied to the LED 202 so as to maintain the amount of light output from the LED 202 at a predetermined level.

At Step S517 following next, the printer controller 2090 acquires an output signal of the photodiode 209, and acquires the amount of light received by the photodiode 209. Hereinafter, the amount of received light thus acquired is referred to as an "amount of light received for the reference light", for convenience.

At Step S519 following next, the printer controller 2090 turns off the LED 202.

At Step S521 following next, the printer controller 2090 corrects the "amount of light received for the water-absorbed wavelength light" based on the "amount of light received for the reference light". In this embodiment, the printer controller 2090 calculates the "amount of light received for the water-absorbed wavelength light" divided by the "amount of light received for the reference light". Hereinafter, the calculation result is also referred to as a "reference-corrected light amount", for convenience.

At Step S523 following next, the printer controller 2090 corrects the "reference-corrected light amount" further, based on the paper type identified in the paper-type determining process and stored in the RAM.

The equation of the Lambert-Beer law can be rewritten to Equation (4) below. Where, $I_h$ is the reference-corrected light amount, and K is a correction coefficient.

$$I/I_h = \exp(K \cdot N_d) \quad (4)$$

In the embodiment, the correction coefficient K is determined in advance for each of the brands of recording sheet brands that are usable in the color printer 2000. This is achieved by acquiring the moisture content ratio of the recording sheets using the loss-on-drying and detecting the intensity of scattered light using the moisture sensor 2246 while changing the humidity in a range between 40 percent and 80 percent in granularity of 5 percent using an environment tester, and substituting the detection results into Equation (4). The correction coefficient K for each of the brands of recording sheets is then stored in the ROM in the printer controller 2090 as a "correction coefficient table".

In this embodiment, the printer controller 2090 acquires a correction coefficient K corresponding to the paper type identified in the paper-type determining process by referring to the correction coefficient table.

At Step S525 following next, the printer controller 2090 calculates a moisture content ratio $N_d$ from Equation (4) using the reference-corrected light amount and the correction coefficient K. The printer controller 2090 then ends the moisture content ratio detecting process.

Subsequently, the printer controller 2090 acquires the most appropriate development conditions and transfer conditions from the development and transfer table based on the paper type thus identified and the moisture content ratio thus detected.

The printer controller 2090 then controls the developing unit and the transfer unit included in each of the stations based on the most appropriate development conditions and transfer conditions. For example, the printer controller 2090 controls the transfer voltage or the amount of toner. In this manner, high quality images are formed on the recording sheet.

In this embodiment, the water content sensor 2246 is positioned near a plurality of recording sheets stacked in the paper feed tray 2060. In such an arrangement, the topmost recording sheet is allowed to be irradiated with light, and the water content sensor 2246 is allowed to receive the internally scattered light from several sheets below. In this manner, the detection precision of the moisture content ratio can be improved. Furthermore, in this configuration, because the position of the recording sheet irradiated with light is kept constant at any detection timing, fluctuations of the detection results can be reduced. The detection precision can be further improved by taking an average of a plurality of moisture content ratios detected at different timing, or taking an average of output signals of the water content sensor 2246.

As may have become clear from the explanation, in the color printer 2000 according to the embodiment, the paper-type determining sensor 2245, the moisture sensor 2246, and the printer controller 2090 together realize the moisture detector according to the present invention. Furthermore, the paper-type determining sensor 2245 and the printer controller 2090 together realize a paper-type determining unit according to the present invention.

As described above, the moisture sensor according to the embodiment includes the LED 201 outputting water-absorbed wavelength light, the LED 202 outputting the reference light, the optical system on which the light from each of the LEDs is incident, from which linearly polarized light in a first polarization direction comes out to a direction traveling toward an object, on which the light scattered on the object is incident, and from which linearly polarized light having a second polarization direction perpendicularly intersecting with the first polarization direction comes out to a direction other than the direction traveling toward the object, and the photodiode 209 that receives the linear polarized light having the second polarization direction output from the optical system.

Such a configuration enables the photodiode 209 to selectively receive the internally scattered light resulting from light output from the LED 201 and with which the object is irradiated, and traveled back from deep inside of the object. The internally scattered light is very likely to contact with water molecules in the object, because the optical path length in the object is long. Therefore, the light amount of the internally scattered light received by the photodiode 209 is affected by the moisture in the object. In other words, the signal output from the photodiode 209 for receiving the internally scattered light includes information about moisture content of the object. Therefore, a moisture content ratio in the object can be acquired from the output signal from the photodiode 209 in a highly sensitive manner.

Furthermore, the signal output from the photodiode 209 when the object is irradiated with the water-absorbed wavelength light is corrected based on the signal output from the photodiode 209 when the object is irradiated with the reference light. In this manner, the detection precision can be improved.

Furthermore, because the water-absorbed wavelength light traveling toward the object and the reference light traveling toward the object have almost the same optical path, the same area of the object can be irradiated with the water-absorbed wavelength light and with the reference light. In this manner, a correction error can be reduced.

In other words, the moisture sensor according to the embodiment can achieve both of a size reduction and an increased precision.

Furthermore, in the color printer 2000 according to the embodiment, the paper-type determining sensor 2245, the moisture sensor 2246, and the printer controller 2090 detect a moisture content ratio of a recording sheet highly precisely. The printer controller 2090 then acquires the most appropriate development conditions and transfer conditions based on the paper type thus identified and the moisture content ratio thus detected, and controls the developing unit and the transfer unit included in each of the stations based on the most appropriate development conditions and transfer conditions. In this manner, the color printer 2000 is allowed to form high-quality images on a recording sheet in a stable manner.

Explained in the embodiment is an example in which light at a wavelength of 1.45 micrometers is used as the water-absorbed wavelength light, but the present invention is not limited thereto.

Furthermore, explained in the embodiment is an example in which light at a wavelength of 1.3 micrometers is used as the reference light, but the present invention is not limited thereto. Any appropriate wavelengths may be selected depending on objects.

Alternatively, the LEDs may output light at two wavelengths each of which is absorbed by water by different degrees, and one may be used as the water-absorbed wavelength light, and the other may be used as the reference light.

Furthermore, explained in the embodiment is an example in which the housing 210 is made of plastic, but the present invention is not limited thereto. For example, the housing 210 may be made of casted aluminum. In such a case, rigidity of the housing 210 is increased, so that the positional deviation of the optical elements caused by vibrations can be suppressed, and the optical precision can be improved. In addition, in the moisture sensor 2246b and the moisture sensor 2246c in particular, the distance between the object and the condenser lens 212 can be stabilized.

Furthermore, explained in the embodiment is a configuration in which the moisture sensor is disposed near the recording sheets stored in the paper feed tray 2060, but the present invention is not limited thereto.

Furthermore, in the embodiment, a thickness sensor for detecting the thickness of the recording sheet may be further provided, and the printer controller 2090 may refer to a detection result of the thickness sensor when the paper type of the recording sheet is to be determined. Such a configuration enables determination accuracy to be improved.

Furthermore, explained in the embodiment is a configuration in which a paper feed tray is provided in singularity, but the present invention is not limited thereto, and the paper feed tray may be provided in plurality. In such a configuration, the paper-type determining sensor 2245 and the moisture sensor 2246 may be provided for each of the paper feed trays.

Furthermore, in the embodiment, the brand of a recording sheet may be identified while the recording sheet is conveyed. In such a configuration, the paper-type determining sensor 2245 is positioned near a conveying path. For example, the paper-type determining sensor 2245 may be positioned near a conveying path between the paper feeding roller 2054 and the transfer rollers 2042.

Explained in the embodiment is a configuration in which the image forming apparatus is the color printer 2000, but the present invention is not limited thereto, and the image forming apparatus may be an optical plotter or a digital copier, for example.

Furthermore, explained in the embodiment is a configuration in which the image forming apparatus includes four photosensitive drums, but the present invention is not limited thereto.

Furthermore, the moisture sensor 2246 is also applicable to an image forming apparatus that forms an image by spraying ink onto a recording sheet. In such a configuration, the amount of ink sprayed is adjusted based on the moisture content ratio.

The moisture sensor according to the embodiment can achieve a size reduction and a precision increase simultaneously.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A moisture sensor for detecting moisture content of an object, the moisture sensor comprising:
    a light source to emit light including an infrared wavelength that is absorbed by water;
    an optical system to receive the light from the light source and output linearly polarized light having a first polarization direction in a direction toward the object, and to receive light scattered from the object and output linearly polarized light having a second polarization direction perpendicular to the first polarization direction in another direction other than the direction toward the object; and
    a photodetector to receive the linearly polarized light having the second polarization direction output from the optical system.

2. The moisture sensor according to claim 1, wherein
    the optical system includes a first optical member and a second optical member,
    the first optical member is disposed in an optical path of the light output from the light source and outputs the linearly polarized light having the first polarization direction, and
    the second optical member is disposed in an optical path of light that is scattered from the object caused due to the light output from the first optical member, and passes the linearly polarized light having the second polarization direction.

3. The moisture sensor according to claim 1, wherein
    the optical system includes a polarization beam splitter to reflect the linearly polarized light having the first polarization direction included in the light emitted from the light source toward the object and to pass the linearly polarized light having the second polarization direction included in the light scattered from the object toward the photodetector.

4. The moisture sensor according to claim 1, wherein the light source emits first light and second light that differ in light absorption by water from each other, the first light and the second light that are output from the optical system travel in a same optical path toward the object.

5. The moisture sensor according to claim 1, wherein
    the optical system is a confocal optical system including a pair of lenses, and a focal point of one of the lenses is at a surface of the object, and
    the optical system includes a plate member to block a center portion of the scattered light traveling toward the photodetector, the plate member being disposed at a focal point of the other lens.

6. The moisture sensor according to claim 1, wherein the linearly polarized light having the first polarization direction is p-polarized light.

7. A moisture detector for detecting moisture content of paper, the moisture detector comprising:
    the moisture sensor according to claim 1, the object being the paper;
    a paper-type determining unit to determine a type of the paper; and
    a processor to correct an output of the moisture sensor based on a determination result of the paper-type determining unit.

8. An image forming apparatus for forming an image on a recording medium, the image forming apparatus comprising the moisture sensor according to claim 1, the object being the recording medium.

* * * * *